(12) United States Patent
Dunwoody et al.

(10) Patent No.: US 12,738,365 B2
(45) **Date of Patent: *Sep. 15, 2026**

(54) DASHBOARD USAGE TRACKING AND GENERATION OF DASHBOARD RECOMMENDATIONS

(71) Applicant: MONDAY.COM LIMITED, Tel Aviv (IL)

(72) Inventors: Kimberly S. Dunwoody, Parker, CO (US); Susan E. Teague Rector, Denver, CO (US)

(73) Assignee: MONDAY.COM LTD, Tel Aviv (IL)

( * ) Notice: Subject to any disclaimer, the term of this patent is extended or adjusted under 35 U.S.C. 154(b) by 1337 days.

This patent is subject to a terminal disclaimer.

(21) Appl. No.: 17/236,710

(22) Filed: Apr. 21, 2021

(65) Prior Publication Data

US 2021/0241893 A1 Aug. 5, 2021

Related U.S. Application Data

(63) Continuation of application No. 15/470,980, filed on Mar. 28, 2017, now Pat. No. 11,037,674.

(51) Int. Cl.
*G06Q 10/00* (2026.01)
*G06F 16/9535* (2019.01)
(Continued)

(52) U.S. Cl.
CPC ......... *G16H 40/20* (2018.01); *G06F 16/9535* (2019.01); *G06Q 10/00* (2013.01);
(Continued)

(58) Field of Classification Search
CPC .... G16H 40/20; G16H 10/60; G06F 16/9535; G06Q 10/00; G06Q 40/08; G06Q 50/22
See application file for complete search history.

(56) References Cited

U.S. PATENT DOCUMENTS

| | | | |
|---|---|---|---|
| 4,972,314 | A | 11/1990 | Getzinger et al. |
| 5,220,657 | A | 6/1993 | Bly et al. |

(Continued)

FOREIGN PATENT DOCUMENTS

| | | | |
|---|---|---|---|
| CA | 2828011 | A1 | 9/2012 |
| CN | 103064833 | A | 4/2013 |

(Continued)

OTHER PUBLICATIONS

List of IBM Patents or Patent Applications Treated as Related, Jun. 4, 2021, 2 pages.

(Continued)

*Primary Examiner* — Ryan C Vaughn
(74) *Attorney, Agent, or Firm* — FINNEGAN, HENDERSON, FARABOW, GARRETT & DUNNER L.L.P.

(57) ABSTRACT

Mechanisms are provided for generating a dashboard recommendation based on tracked user input patterns and the operation of predictive analytics. The mechanisms present a dashboard interface to a user via a client computing device, and track user inputs to the client computing device at least during and after presentation of the dashboard interface to the user via the client computing device. The mechanisms apply predictive analytics to the tracked user inputs to predict a type of data the user is attempting to access, and correlate the predicted type of data with one or more portions of one or more other dashboard interfaces that provide a representation of data having a type matching the predicted type of data. The mechanisms output a recommendation output to the user via the client computing device recommending the user access the one or more other dashboard interfaces.

24 Claims, 7 Drawing Sheets

(51) Int. Cl.
*G06Q 40/08* (2012.01)
*G06Q 50/22* (2024.01)
*G16H 10/60* (2018.01)
*G16H 40/20* (2018.01)

(52) U.S. Cl.
CPC ............ *G06Q 40/08* (2013.01); *G06Q 50/22* (2013.01); *G16H 10/60* (2018.01)

(56) References Cited

U.S. PATENT DOCUMENTS 5,479,602 A 12/1995 Baecker et al.
5,517,663 A 5/1996 Kahn
5,632,009 A 5/1997 Rao et al.
5,657,437 A 8/1997 Bishop et al.
5,682,469 A 10/1997 Linnett et al.
5,696,702 A 12/1997 Skinner et al.
5,726,701 A 3/1998 Needham
5,734,837 A 3/1998 Flores et al.
5,787,411 A 7/1998 Groff et al.
5,880,742 A 3/1999 Rao et al.
5,933,145 A 8/1999 Meek
5,999,911 A 12/1999 Berg et al.
6,016,438 A 1/2000 Wakayama
6,016,553 A 1/2000 Schneider et al.
6,023,695 A 2/2000 Osborn et al.
6,034,681 A 3/2000 Miller et al.
6,049,622 A 4/2000 Robb et al.
6,088,707 A 7/2000 Bates et al.
6,108,573 A 8/2000 Debbins et al.
6,111,573 A 8/2000 Mccomb et al.
6,157,381 A 12/2000 Bates et al.
6,167,405 A 12/2000 Rosensteel et al.
6,169,534 B1 1/2001 Raffel et al.
6,182,127 B1 1/2001 Cronin, III et al.
6,185,582 B1 2/2001 Zellweger et al.
6,195,794 B1 2/2001 Buxton
6,222,541 B1 4/2001 Bates et al.
6,252,594 B1 6/2001 Xia et al.
6,266,067 B1 7/2001 Owen et al.
6,275,809 B1 8/2001 Tamaki et al.
6,330,022 B1 12/2001 Seligmann
6,377,965 B1 4/2002 Fries et al.
6,385,617 B1 5/2002 Malik
6,460,043 B1 10/2002 Tabbara et al.
6,496,832 B2 12/2002 Chi et al.
6,509,912 B1 1/2003 Moran et al.
6,510,459 B2 1/2003 Cronin et al.
6,522,347 B1 2/2003 Tsuji et al.
6,527,556 B1 3/2003 Koskinen
6,567,830 B1 5/2003 Madduri
6,606,740 B1 8/2003 Lynn et al.
6,626,959 B1 9/2003 Moise et al.
6,636,242 B2 10/2003 Bowman-Amuah
6,647,370 B1 11/2003 Fu et al.
6,661,431 B1 12/2003 Stuart et al.
6,874,010 B1 3/2005 Sargent
6,988,248 B1 1/2006 Tang et al.
7,027,997 B1 4/2006 Robinson et al.
7,034,860 B2 4/2006 Lia et al.
7,043,529 B1 5/2006 Simonoff
7,054,891 B2 5/2006 Cole
7,228,492 B1 6/2007 Graham
7,237,188 B1 6/2007 Leung
7,249,042 B1 7/2007 Doerr et al.
7,272,637 B1 9/2007 Himmelstein
7,274,375 B1 9/2007 David
7,379,934 B1 5/2008 Forman et al.
7,380,202 B1 5/2008 Lindhorst et al.
7,383,320 B1 6/2008 Silberstein et al.
7,389,473 B1 6/2008 Sawicki et al.
7,415,664 B2 8/2008 Aureglia et al.
7,417,644 B2 8/2008 Cooper et al.
7,461,077 B1 12/2008 Greenwood
7,464,366 B2 12/2008 Shukla et al.
7,489,976 B2 2/2009 Adra
7,565,270 B2 7/2009 Bramwell et al.
7,617,443 B2 11/2009 Mills et al.
7,685,152 B2 3/2010 Chivukula et al.
7,707,514 B2 4/2010 Forstall et al.
7,710,290 B2 5/2010 Johnson
7,747,782 B2 6/2010 Hunt et al.
7,770,100 B2 8/2010 Chamberlain et al.
7,827,476 B1 11/2010 Roberts et al.
7,827,615 B1 11/2010 Allababidi et al.
7,836,408 B1 11/2010 Ollmann et al.
7,916,157 B1 3/2011 Kelley et al.
7,921,360 B1 4/2011 Sundermeyer et al.
7,933,952 B2 4/2011 Parker et al.
7,945,622 B1 5/2011 Pegg
7,954,043 B2 5/2011 Bera
7,954,064 B2 5/2011 Forstall et al.
8,046,703 B2 10/2011 Busch et al.
8,060,518 B2 11/2011 Timmons
8,078,955 B1 12/2011 Gupta
8,082,274 B2 12/2011 Steinglass et al.
8,108,241 B2 1/2012 Shukoor
8,136,031 B2 3/2012 Massand
8,151,213 B2 4/2012 Weitzman et al.
8,223,172 B1 7/2012 Miller et al.
8,286,072 B2 10/2012 Chamberlain et al.
8,365,095 B2 1/2013 Bansal et al.
8,375,327 B2 2/2013 Lorch et al.
8,386,960 B1 2/2013 Eismann et al.
8,407,217 B1 3/2013 Zhang
8,413,261 B2 4/2013 Nemoy et al.
8,423,909 B2 4/2013 Zabielski
8,543,566 B2 9/2013 Weissman et al.
8,548,997 B1 10/2013 Wu
8,560,942 B2 10/2013 Fortes et al.
8,566,732 B2 10/2013 Louch et al.
8,572,173 B2 10/2013 Briere et al.
8,578,399 B2 11/2013 Khen et al.
8,601,383 B2 12/2013 Folting et al.
8,620,703 B1 12/2013 Kapoor et al.
8,621,652 B2 12/2013 Slater
8,635,520 B2 1/2014 Christiansen et al.
8,660,881 B2 2/2014 Wood et al.
8,677,448 B1 3/2014 Kauffman et al.
8,689,131 B2 4/2014 Ali et al.
8,694,981 B2 4/2014 Federighi et al.
8,719,071 B2 5/2014 MacIntyre et al.
8,738,414 B1 5/2014 Nagar et al.
8,812,471 B2 8/2014 Akita
8,819,042 B2 8/2014 Samudrala et al.
8,825,758 B2 9/2014 Bailor et al.
8,838,533 B2 9/2014 Kwiatkowski et al.
8,862,979 B2 10/2014 Hawking
8,863,022 B2 10/2014 Rhodes et al.
8,869,027 B2 10/2014 Louch et al.
8,937,627 B1 1/2015 Otero et al.
8,938,465 B2 1/2015 Messer
8,954,871 B2 2/2015 Louch et al.
9,007,405 B1 4/2015 Eldar et al.
9,015,716 B2 4/2015 Fletcher et al.
9,021,118 B2 4/2015 John et al.
9,026,897 B2 5/2015 Zarras
9,043,362 B2 5/2015 Weissman et al.
9,063,958 B2 6/2015 Muller et al.
9,129,234 B2 9/2015 Campbell et al.
9,159,246 B2 10/2015 Rodriguez et al.
9,172,738 B1 10/2015 Dacosta
9,177,238 B2 11/2015 Windmueller et al.
9,183,303 B1 11/2015 Goel et al.
9,223,770 B1 12/2015 Ledet
9,239,719 B1 1/2016 Feinstein et al.
9,244,917 B1 1/2016 Sharma et al.
9,253,130 B2 2/2016 Zaveri
9,268,604 B1 2/2016 Herzberg et al.
9,286,246 B2 3/2016 Saito et al.
9,286,475 B2 3/2016 Li et al.
9,292,587 B2 3/2016 Kann et al.
9,336,502 B2 5/2016 Mohammad et al.
9,342,579 B2 5/2016 Cao et al.

(56) References Cited

U.S. PATENT DOCUMENTS

| | | | |
|---|---|---|---|
| 9,361,287 | B1 | 6/2016 | Simon et al. |
| 9,372,592 | B1 | 6/2016 | Goodspeed et al. |
| 9,390,059 | B1 | 7/2016 | Gur et al. |
| 9,395,959 | B2 | 7/2016 | Hatfield et al. |
| 9,424,287 | B2 | 8/2016 | Schroth |
| 9,424,333 | B1 | 8/2016 | Bisignani et al. |
| 9,424,545 | B1 | 8/2016 | Lee |
| 9,430,458 | B2 | 8/2016 | Rhee et al. |
| 9,449,031 | B2 | 9/2016 | Barrus et al. |
| 9,495,386 | B2 | 11/2016 | Tapley et al. |
| 9,519,699 | B1 | 12/2016 | Kulkarni et al. |
| 9,536,197 | B1 | 1/2017 | Penilla et al. |
| 9,558,172 | B2 | 1/2017 | Rampson et al. |
| 9,569,511 | B2 | 2/2017 | Morin |
| 9,613,086 | B1 | 4/2017 | Sherman |
| 9,635,091 | B1 | 4/2017 | Laukkanen et al. |
| 9,659,284 | B1 | 5/2017 | Wilson et al. |
| 9,679,456 | B2 | 6/2017 | East |
| 9,686,086 | B1 | 6/2017 | Nguyen et al. |
| 9,720,602 | B1 | 8/2017 | Chen et al. |
| 9,727,376 | B1 | 8/2017 | Bills et al. |
| 9,760,271 | B2 | 9/2017 | Persaud |
| 9,779,150 | B1 | 10/2017 | Sherman et al. |
| 9,794,256 | B2 | 10/2017 | Kiang et al. |
| 9,798,829 | B1 | 10/2017 | Baisley |
| 9,811,676 | B1 | 11/2017 | Gauvin |
| 9,866,561 | B2 | 1/2018 | Psenka et al. |
| 9,870,136 | B2 | 1/2018 | Pourshahid |
| 9,911,092 | B2 | 3/2018 | Goja |
| 10,001,908 | B2 | 6/2018 | Grieve et al. |
| 10,043,296 | B2 | 8/2018 | Li |
| 10,057,246 | B1 | 8/2018 | Drozd et al. |
| 10,067,928 | B1 | 9/2018 | Krappe |
| 10,078,668 | B1 | 9/2018 | Woodrow et al. |
| 10,169,306 | B2 | 1/2019 | O'Shaughnessy et al. |
| 10,176,154 | B2 | 1/2019 | Ben-Aharon et al. |
| 10,235,441 | B1 | 3/2019 | Makhlin et al. |
| 10,255,609 | B2 | 4/2019 | Kinkead et al. |
| 10,282,405 | B1 | 5/2019 | Silk et al. |
| 10,282,406 | B2 | 5/2019 | Bissantz |
| 10,311,080 | B2 | 6/2019 | Folting et al. |
| 10,318,624 | B1 | 6/2019 | Rosner et al. |
| 10,327,712 | B2 | 6/2019 | Beymer et al. |
| 10,347,017 | B2 | 7/2019 | Ruble et al. |
| 10,372,706 | B2 | 8/2019 | Chavan et al. |
| 10,380,140 | B2 | 8/2019 | Sherman |
| 10,419,469 | B1 | 9/2019 | Singh et al. |
| 10,423,758 | B2 | 9/2019 | Kido et al. |
| 10,445,702 | B1 | 10/2019 | Hunt |
| 10,452,360 | B1 | 10/2019 | Burman et al. |
| 10,453,118 | B2 | 10/2019 | Smith et al. |
| 10,474,317 | B2 | 11/2019 | Ramanathan et al. |
| 10,489,391 | B1 | 11/2019 | Tomlin |
| 10,489,462 | B1 | 11/2019 | Rogynskyy et al. |
| 10,496,737 | B1 | 12/2019 | Sayre et al. |
| 10,505,825 | B1 | 12/2019 | Bettaiah et al. |
| 10,528,599 | B1 | 1/2020 | Pandis et al. |
| 10,534,507 | B1 | 1/2020 | Laukkanen et al. |
| 10,540,152 | B1 | 1/2020 | Krishnaswamy et al. |
| 10,540,434 | B2 | 1/2020 | Migeon et al. |
| 10,546,001 | B1 | 1/2020 | Nguyen et al. |
| 10,564,622 | B1 | 2/2020 | Dean et al. |
| 10,573,407 | B2 | 2/2020 | Ginsburg |
| 10,579,724 | B2 | 3/2020 | Campbell et al. |
| 10,581,675 | B1 | 3/2020 | Iyer et al. |
| 10,587,714 | B1 | 3/2020 | Kulkarni et al. |
| 10,628,002 | B1 | 4/2020 | Kang et al. |
| 10,698,594 | B2 | 6/2020 | Sanches et al. |
| 10,706,061 | B2 | 7/2020 | Sherman et al. |
| 10,719,220 | B2 | 7/2020 | Ouellet et al. |
| 10,719,311 | B2 | 7/2020 | Foskett et al. |
| 10,733,256 | B2 | 8/2020 | Fickenscher et al. |
| 10,740,117 | B2 | 8/2020 | Ording et al. |
| 10,747,764 | B1 | 8/2020 | Plenderleith |
| 10,747,950 | B2 | 8/2020 | Dang et al. |
| 10,748,312 | B2 | 8/2020 | Ruble et al. |
| 10,754,688 | B2 | 8/2020 | Powell |
| 10,761,691 | B2 | 9/2020 | Anzures et al. |
| 10,762,471 | B1 | 9/2020 | Wang et al. |
| 10,795,555 | B2 | 10/2020 | Burke et al. |
| 10,795,649 | B1 | 10/2020 | Drake et al. |
| 10,809,696 | B1 | 10/2020 | Principato |
| 10,817,660 | B2 | 10/2020 | Rampson et al. |
| D910,077 | S | 2/2021 | Naroshevitch et al. |
| 10,955,992 | B2 | 3/2021 | Hooton et al. |
| 10,963,578 | B2 | 3/2021 | More et al. |
| 10,997,531 | B2 | 5/2021 | Leonelli et al. |
| 11,010,371 | B1 | 5/2021 | Slomka et al. |
| 11,030,259 | B2 | 6/2021 | Mullins et al. |
| 11,042,363 | B1 | 6/2021 | Krishnaswamy et al. |
| 11,042,699 | B1 | 6/2021 | Sayre et al. |
| 11,044,257 | B1 | 6/2021 | Heuts et al. |
| 11,048,499 | B2 | 6/2021 | Foskett et al. |
| 11,048,714 | B2 | 6/2021 | Sherman et al. |
| 11,080,636 | B1 | 8/2021 | Son |
| 11,086,894 | B1 | 8/2021 | Srivastava et al. |
| 11,128,464 | B1 | 9/2021 | Loladia |
| 11,144,854 | B1 | 10/2021 | Mouawad |
| 11,182,218 | B2 | 11/2021 | Sanchez et al. |
| 11,190,516 | B1 | 11/2021 | Loladia |
| 11,222,167 | B2 | 1/2022 | Gehrmann et al. |
| 11,231,862 | B1 | 1/2022 | Vig et al. |
| 11,240,278 | B1 | 2/2022 | Wang et al. |
| 11,243,688 | B1 | 2/2022 | Remy et al. |
| 11,301,623 | B2 | 4/2022 | Helft et al. |
| 11,341,705 | B1 | 5/2022 | Isaacs et al. |
| 11,356,485 | B2 | 6/2022 | Hegde et al. |
| 11,360,765 | B2 | 6/2022 | Miller et al. |
| 11,405,504 | B1 | 8/2022 | Tripathy et al. |
| 11,429,384 | B1 | 8/2022 | Navert et al. |
| 11,443,390 | B1 | 9/2022 | Caligaris et al. |
| 11,481,092 | B2 * | 10/2022 | Roy ...................... G06N 20/00 |
| 11,494,171 | B1 | 11/2022 | Acharya et al. |
| 11,513,772 | B1 | 11/2022 | Gross |
| 11,570,182 | B1 | 1/2023 | Tran et al. |
| 11,593,096 | B1 | 2/2023 | Chaptini et al. |
| 11,593,477 | B1 | 2/2023 | Thimmegowda et al. |
| 11,620,615 | B2 | 4/2023 | Jiang et al. |
| 11,681,445 | B2 | 6/2023 | Vohra et al. |
| 11,682,091 | B2 | 6/2023 | Sukman et al. |
| 11,720,410 | B2 | 8/2023 | Culp et al. |
| 11,750,475 | B1 | 9/2023 | Gonzalez et al. |
| 11,799,951 | B1 | 10/2023 | Maloo et al. |
| 11,823,269 | B2 | 11/2023 | Aisen et al. |
| 11,882,117 | B1 | 1/2024 | Kumar |
| 11,922,222 | B1 | 3/2024 | Chawla et al. |
| 11,977,858 | B2 | 5/2024 | Kulkarni et al. |
| 12,034,613 | B2 | 7/2024 | Gupta et al. |
| 12,094,018 | B1 | 9/2024 | O'Malley |
| 12,105,939 | B1 | 10/2024 | Rank et al. |
| 2001/0008998 | A1 | 7/2001 | Tamaki et al. |
| 2001/0032248 | A1 | 10/2001 | Krafchin |
| 2001/0039551 | A1 | 11/2001 | Saito et al. |
| 2002/0002459 | A1 | 1/2002 | Lewis et al. |
| 2002/0019827 | A1 | 2/2002 | Shiman et al. |
| 2002/0065848 | A1 | 5/2002 | Walker et al. |
| 2002/0065849 | A1 | 5/2002 | Ferguson et al. |
| 2002/0065880 | A1 | 5/2002 | Hasegawa et al. |
| 2002/0069207 | A1 | 6/2002 | Alexander et al. |
| 2002/0075309 | A1 | 6/2002 | Michelman et al. |
| 2002/0082892 | A1 | 6/2002 | Raffel et al. |
| 2002/0099777 | A1 | 7/2002 | Gupta et al. |
| 2002/0138528 | A1 | 9/2002 | Gong et al. |
| 2003/0004771 | A1 | 1/2003 | Yaung |
| 2003/0033196 | A1 | 2/2003 | Tomlin |
| 2003/0041113 | A1 | 2/2003 | Larsen |
| 2003/0051377 | A1 | 3/2003 | Chirafesi |
| 2003/0052912 | A1 | 3/2003 | Bowman et al. |
| 2003/0058277 | A1 | 3/2003 | Bowman-Amuah |
| 2003/0065662 | A1 | 4/2003 | Cosic |
| 2003/0093408 | A1 | 5/2003 | Brown et al. |
| 2003/0101416 | A1 | 5/2003 | McInnes et al. |
| 2003/0135558 | A1 | 7/2003 | Bellotti et al. |
| 2003/0137536 | A1 | 7/2003 | Hugh |

(56) References Cited

U.S. PATENT DOCUMENTS

2003/0187864 A1 10/2003 McGoveran
2003/0200215 A1 10/2003 Chen et al.
2003/0204490 A1 10/2003 Kasriel
2003/0233224 A1 12/2003 Marchisio et al.
2004/0010514 A1 1/2004 Agarwal et al.
2004/0032432 A1 2/2004 Baynger
2004/0078105 A1 4/2004 Moon et al.
2004/0078373 A1 4/2004 Ghoneimy et al.
2004/0098284 A1 5/2004 Petito et al.
2004/0111666 A1 6/2004 Hollcraft
2004/0119713 A1 6/2004 Meyringer
2004/0133441 A1 7/2004 Brady et al.
2004/0138939 A1 7/2004 Theiler
2004/0139400 A1 7/2004 Allam et al.
2004/0162833 A1 8/2004 Jones et al.
2004/0172592 A1 9/2004 Collie et al.
2004/0212615 A1 10/2004 Uthe
2004/0215443 A1 10/2004 Hatton
2004/0230940 A1 11/2004 Cooper et al.
2004/0268227 A1 12/2004 Brid
2005/0010454 A1 1/2005 Falk et al.
2005/0010582 A1* 1/2005 Saito .................... G06F 16/284
2005/0034058 A1 2/2005 Mills et al.
2005/0034064 A1 2/2005 Meyers et al.
2005/0039001 A1 2/2005 Hudis et al.
2005/0039033 A1 2/2005 Meyers et al.
2005/0044486 A1 2/2005 Kotler et al.
2005/0060342 A1 3/2005 Farag
2005/0063615 A1 3/2005 Siegel et al.
2005/0066306 A1 3/2005 Diab
2005/0086360 A1 4/2005 Mamou et al.
2005/0091314 A1 4/2005 Blagsvedt et al.
2005/0091596 A1 4/2005 Anthony et al.
2005/0096973 A1 5/2005 Heyse et al.
2005/0114305 A1 5/2005 Haynes et al.
2005/0125395 A1 6/2005 Boettiger
2005/0149908 A1 7/2005 Klianev
2005/0165600 A1 7/2005 Kasravi et al.
2005/0171881 A1 8/2005 Ghassemieh et al.
2005/0210371 A1 9/2005 Pollock et al.
2005/0216830 A1 9/2005 Turner et al.
2005/0228250 A1 10/2005 Bitter et al.
2005/0251021 A1 11/2005 Kaufman et al.
2005/0257204 A1 11/2005 Bryant et al.
2005/0278297 A1 12/2005 Nelson
2005/0289170 A1 12/2005 Brown et al.
2005/0289342 A1 12/2005 Needham et al.
2005/0289453 A1 12/2005 Segal et al.
2006/0009960 A1 1/2006 Valencot et al.
2006/0013462 A1 1/2006 Sadikali
2006/0015499 A1 1/2006 Clissold et al.
2006/0015806 A1 1/2006 Wallace
2006/0031148 A1 2/2006 O'Dell et al.
2006/0031764 A1 2/2006 Keyser et al.
2006/0036568 A1 2/2006 Moore et al.
2006/0047553 A1 3/2006 Fuhrmann et al.
2006/0047811 A1 3/2006 Lau et al.
2006/0053096 A1 3/2006 Subramanian et al.
2006/0053194 A1 3/2006 Schneider et al.
2006/0069604 A1 3/2006 Leukart et al.
2006/0069635 A1 3/2006 Ram et al.
2006/0074735 A1 4/2006 Shukla et al.
2006/0080594 A1 4/2006 Chavoustie et al.
2006/0085744 A1 4/2006 Hays et al.
2006/0090169 A1 4/2006 Daniels et al.
2006/0095276 A1 5/2006 Axelrod et al.
2006/0101324 A1 5/2006 Goldberg et al.
2006/0106642 A1 5/2006 Reicher et al.
2006/0107196 A1 5/2006 Thanu et al.
2006/0111953 A1 5/2006 Setya
2006/0112123 A1 5/2006 Clark et al.
2006/0129415 A1 6/2006 Thukral et al.
2006/0129913 A1 6/2006 Vigesaa et al.
2006/0136828 A1 6/2006 Asano
2006/0150090 A1 7/2006 Swamidass
2006/0173762 A1 8/2006 Clater
2006/0173908 A1 8/2006 Browning et al.
2006/0190313 A1 8/2006 Lu
2006/0190822 A1* 8/2006 Basson ................. G06Q 10/10
715/765
2006/0212299 A1 9/2006 Law
2006/0224542 A1 10/2006 Yalamanchi
2006/0224568 A1 10/2006 Debrito
2006/0224946 A1 10/2006 Barrett et al.
2006/0236246 A1 10/2006 Bono et al.
2006/0250369 A1 11/2006 Keim
2006/0253205 A1 11/2006 Gardiner
2006/0271574 A1 11/2006 Villaron et al.
2006/0282348 A1 12/2006 Greenfield et al.
2006/0287998 A1 12/2006 Folting et al.
2006/0294451 A1 12/2006 Kelkar et al.
2007/0027932 A1 2/2007 Thibeault
2007/0032993 A1 2/2007 Yamaguchi et al.
2007/0033531 A1 2/2007 Marsh
2007/0050322 A1 3/2007 Vigesaa et al.
2007/0050379 A1 3/2007 Day et al.
2007/0050710 A1 3/2007 Redekop
2007/0067373 A1 3/2007 Higgins et al.
2007/0073899 A1 3/2007 Judge et al.
2007/0092048 A1 4/2007 Chelstrom et al.
2007/0094607 A1 4/2007 Morgan et al.
2007/0101291 A1 5/2007 Forstall et al.
2007/0106754 A1 5/2007 Moore
2007/0118527 A1 5/2007 Winje et al.
2007/0118813 A1 5/2007 Forstall et al.
2007/0143169 A1 6/2007 Grant et al.
2007/0143736 A1 6/2007 Moriarty et al.
2007/0150389 A1 6/2007 Aamodt et al.
2007/0168861 A1 7/2007 Bell et al.
2007/0174228 A1 7/2007 Folting et al.
2007/0174760 A1 7/2007 Chamberlain et al.
2007/0186173 A1 8/2007 Both et al.
2007/0192729 A1 8/2007 Downs
2007/0220119 A1 9/2007 Himmelstein
2007/0233647 A1 10/2007 Rawat et al.
2007/0239746 A1 10/2007 Masselle et al.
2007/0256043 A1 11/2007 Peters et al.
2007/0282522 A1 12/2007 Geelen
2007/0282627 A1 12/2007 Greenstein et al.
2007/0283259 A1 12/2007 Barry et al.
2007/0294235 A1 12/2007 Millett
2007/0299795 A1 12/2007 Macbeth et al.
2007/0300174 A1 12/2007 Macbeth et al.
2007/0300185 A1 12/2007 Macbeth et al.
2008/0004929 A9 1/2008 Raffel et al.
2008/0005235 A1 1/2008 Hegde et al.
2008/0010615 A1 1/2008 Curtis et al.
2008/0033777 A1 2/2008 Shukoor
2008/0034307 A1 2/2008 Cisler et al.
2008/0034314 A1 2/2008 Louch et al.
2008/0040181 A1 2/2008 Freire et al.
2008/0052291 A1 2/2008 Bender
2008/0059312 A1 3/2008 Gern et al.
2008/0059539 A1 3/2008 Chin et al.
2008/0065460 A1 3/2008 Raynor
2008/0077530 A1 3/2008 Banas et al.
2008/0097748 A1 4/2008 Haley et al.
2008/0104091 A1 5/2008 Chin
2008/0126389 A1 5/2008 Mush et al.
2008/0126945 A1 5/2008 Munkvold et al.
2008/0127205 A1 5/2008 Barros
2008/0133736 A1 6/2008 Wensley et al.
2008/0148140 A1 6/2008 Nakano
2008/0155547 A1 6/2008 Weber et al.
2008/0163075 A1 7/2008 Beck et al.
2008/0183593 A1 7/2008 Dierks
2008/0195948 A1 8/2008 Bauer
2008/0209318 A1 8/2008 Allsop et al.
2008/0216022 A1 9/2008 Lorch et al.
2008/0222192 A1 9/2008 Hughes
2008/0256014 A1 10/2008 Gould et al.
2008/0256429 A1 10/2008 Penner et al.
2008/0270597 A1 10/2008 Tenenti
2008/0282189 A1 11/2008 Hofmann et al.

(56) References Cited

U.S. PATENT DOCUMENTS

2008/0295038 A1 11/2008 Helfman et al.
2008/0301237 A1 12/2008 Parsons et al.
2009/0006171 A1 1/2009 Blatchley et al.
2009/0006283 A1 1/2009 Labrie et al.
2009/0007157 A1 1/2009 Ward et al.
2009/0013244 A1 1/2009 Cudich et al.
2009/0019383 A1 1/2009 Riley et al.
2009/0024944 A1 1/2009 Louch et al.
2009/0043814 A1 2/2009 Faris et al.
2009/0044090 A1 2/2009 Gur et al.
2009/0048896 A1 2/2009 Anandan
2009/0049372 A1 2/2009 Goldberg
2009/0075694 A1 3/2009 Kim et al.
2009/0077164 A1 3/2009 Phillips et al.
2009/0077217 A1 3/2009 McFarland et al.
2009/0083140 A1 3/2009 Phan
2009/0088875 A1 4/2009 Baier et al.
2009/0094514 A1 4/2009 Dargahi et al.
2009/0113310 A1 4/2009 Appleyard et al.
2009/0129596 A1 5/2009 Chavez et al.
2009/0132331 A1 5/2009 Cartledge et al.
2009/0132470 A1 5/2009 Vignet
2009/0150813 A1 6/2009 Chang et al.
2009/0174680 A1 7/2009 Anzures et al.
2009/0192787 A1 7/2009 Roon
2009/0198715 A1 8/2009 Barbarek
2009/0222760 A1 9/2009 Halverson et al.
2009/0234699 A1 9/2009 Steinglass et al.
2009/0240647 A1 9/2009 Green et al.
2009/0248710 A1 10/2009 Mccormack et al.
2009/0256972 A1 10/2009 Ramaswamy et al.
2009/0262690 A1 10/2009 Breuer et al.
2009/0271696 A1 10/2009 Bailor et al.
2009/0276692 A1 11/2009 Rosner
2009/0292690 A1 11/2009 Culbert
2009/0313201 A1 12/2009 Huelsman et al.
2009/0313537 A1 12/2009 Fu et al.
2009/0313570 A1 12/2009 Po
2009/0319623 A1 12/2009 Srinivasan et al.
2009/0319882 A1 12/2009 Morrison et al.
2009/0327240 A1 12/2009 Meehan et al.
2009/0327301 A1 12/2009 Lees et al.
2009/0327851 A1 12/2009 Raposo
2009/0327875 A1 12/2009 Kinkoh
2010/0017699 A1 1/2010 Farrell et al.
2010/0031135 A1 2/2010 Naghshin et al.
2010/0057646 A1 3/2010 Martin et al.
2010/0070845 A1 3/2010 Facemire et al.
2010/0070895 A1 3/2010 Messer
2010/0077260 A1 3/2010 Pillai et al.
2010/0082705 A1 4/2010 Ramesh et al.
2010/0083164 A1 4/2010 Martin et al.
2010/0088636 A1 4/2010 Yerkes et al.
2010/0095219 A1 4/2010 Stachowiak et al.
2010/0095298 A1 4/2010 Seshadrinathan et al.
2010/0100427 A1 4/2010 Mckeown et al.
2010/0100463 A1 4/2010 Molotsi et al.
2010/0114926 A1 5/2010 Agrawal et al.
2010/0149005 A1 6/2010 Yoon et al.
2010/0174678 A1 7/2010 Massand
2010/0205521 A1 8/2010 Folting
2010/0228752 A1 9/2010 Folting et al.
2010/0241477 A1 9/2010 Nylander et al.
2010/0241948 A1 9/2010 Andeen et al.
2010/0241968 A1 9/2010 Tarara et al.
2010/0241972 A1 9/2010 Spataro et al.
2010/0241990 A1 9/2010 Gabriel et al.
2010/0251090 A1 9/2010 Chamberlain et al.
2010/0251386 A1 9/2010 Gilzean et al.
2010/0257015 A1 10/2010 Molander
2010/0262625 A1 10/2010 Pittenger
2010/0268705 A1 10/2010 Douglas et al.
2010/0268773 A1 10/2010 Hunt et al.
2010/0281462 A1 11/2010 Festa
2010/0287163 A1 11/2010 Sridhar et al.
2010/0287221 A1 11/2010 Battepati et al.
2010/0313119 A1 12/2010 Baldwin et al.
2010/0324964 A1 12/2010 Callanan et al.
2010/0332973 A1 12/2010 Kloiber et al.
2011/0010340 A1 1/2011 Hung et al.
2011/0016432 A1 1/2011 Helfman
2011/0028138 A1 2/2011 Davies-Moore et al.
2011/0047484 A1 2/2011 Mount et al.
2011/0055177 A1 3/2011 Chakra et al.
2011/0066933 A1 3/2011 Ludwig
2011/0071869 A1 3/2011 O'Brien et al.
2011/0106636 A1 5/2011 Spear et al.
2011/0119352 A1 5/2011 Perov et al.
2011/0154192 A1 6/2011 Yang et al.
2011/0179371 A1 7/2011 Kopycinski et al.
2011/0205231 A1 8/2011 Hartley et al.
2011/0208324 A1 8/2011 Fukatsu
2011/0208732 A1 8/2011 Melton et al.
2011/0209150 A1 8/2011 Hammond et al.
2011/0219321 A1 9/2011 Gonzalez Veron et al.
2011/0225500 A1 9/2011 Casalaina et al.
2011/0225525 A1 9/2011 Chasman et al.
2011/0231273 A1 9/2011 Buchheit
2011/0238716 A1 9/2011 Amir et al.
2011/0258040 A1 10/2011 Gnanasambandam
2011/0269424 A1 11/2011 Multer
2011/0288900 A1 11/2011 Mcqueen et al.
2011/0289397 A1 11/2011 Eastmond et al.
2011/0289439 A1 11/2011 Jugel
2011/0298618 A1 12/2011 Stahl et al.
2011/0302003 A1 12/2011 Shirish et al.
2012/0029962 A1 2/2012 Podgurny et al.
2012/0035974 A1 2/2012 Seybold
2012/0036423 A1 2/2012 Haynes et al.
2012/0036462 A1 2/2012 Schwartz et al.
2012/0050802 A1 3/2012 Masuda
2012/0066587 A1 3/2012 Zhou et al.
2012/0072821 A1 3/2012 Bowling
2012/0079408 A1 3/2012 Rohwer
2012/0081762 A1 4/2012 Yamada
2012/0084798 A1 4/2012 Reeves et al.
2012/0086716 A1 4/2012 Reeves et al.
2012/0086717 A1 4/2012 Liu
2012/0089610 A1 4/2012 Agrawal et al.
2012/0089914 A1 4/2012 Holt et al.
2012/0089992 A1 4/2012 Reeves et al.
2012/0096389 A1 4/2012 Flam et al.
2012/0096392 A1 4/2012 Ording et al.
2012/0102432 A1 4/2012 Breedvelt-Schouten et al.
2012/0102543 A1 4/2012 Kohli et al.
2012/0110515 A1 5/2012 Abramoff et al.
2012/0116834 A1 5/2012 Pope et al.
2012/0116835 A1 5/2012 Pope et al.
2012/0124749 A1 5/2012 Lewman
2012/0130907 A1 5/2012 Thompson et al.
2012/0131445 A1 5/2012 Oyarzabal et al.
2012/0151173 A1 6/2012 Shirley et al.
2012/0158744 A1 6/2012 Tseng et al.
2012/0192050 A1 7/2012 Campbell et al.
2012/0198322 A1 8/2012 Gulwani et al.
2012/0210252 A1 8/2012 Fedoseyeva et al.
2012/0215574 A1 8/2012 Driessnack et al.
2012/0215578 A1 8/2012 Swierz et al.
2012/0229867 A1 9/2012 Takagi
2012/0233150 A1 9/2012 Naim et al.
2012/0233533 A1 9/2012 Yucel et al.
2012/0234907 A1 9/2012 Clark et al.
2012/0236368 A1 9/2012 Uchida et al.
2012/0239454 A1 9/2012 Taix et al.
2012/0244891 A1 9/2012 Appleton
2012/0246170 A1 9/2012 Iantorno
2012/0254252 A1 10/2012 Jin et al.
2012/0254770 A1 10/2012 Ophir
2012/0260190 A1 10/2012 Berger et al.
2012/0278117 A1 11/2012 Nguyen et al.
2012/0284197 A1 11/2012 Sitrick et al.
2012/0284643 A1 11/2012 Sitrick et al.
2012/0297307 A1 11/2012 Rider et al.
2012/0300931 A1 11/2012 Ollikainen et al.

(56) References Cited

U.S. PATENT DOCUMENTS

2012/0303262 A1 11/2012 Alam et al.
2012/0304098 A1 11/2012 Kuulusa
2012/0311496 A1 12/2012 Cao et al.
2012/0311672 A1 12/2012 Connor et al.
2012/0324348 A1 12/2012 Rounthwaite
2013/0015954 A1 1/2013 Thorne et al.
2013/0018952 A1 1/2013 Mcconnell et al.
2013/0018953 A1 1/2013 Mcconnell et al.
2013/0018960 A1 1/2013 Knysz et al.
2013/0024418 A1 1/2013 Sitrick et al.
2013/0024760 A1 1/2013 Vogel et al.
2013/0036369 A1 2/2013 Mitchell et al.
2013/0041958 A1 2/2013 Post et al.
2013/0054514 A1 2/2013 Barrett-Kahn et al.
2013/0055113 A1 2/2013 Chazin et al.
2013/0059598 A1 3/2013 Miyagi et al.
2013/0063490 A1 3/2013 Zaman et al.
2013/0086460 A1 4/2013 Folting et al.
2013/0090969 A1 4/2013 Rivere
2013/0097490 A1 4/2013 Kotler et al.
2013/0103417 A1 4/2013 Seto et al.
2013/0104035 A1 4/2013 Wagner et al.
2013/0111320 A1 5/2013 Campbell et al.
2013/0117268 A1 5/2013 Smith et al.
2013/0151508 A1 6/2013 Kurabayashi et al.
2013/0159832 A1 6/2013 Ingargiola et al.
2013/0159907 A1 6/2013 Brosche et al.
2013/0179209 A1 7/2013 Milosevich
2013/0211866 A1 8/2013 Gordon et al.
2013/0212197 A1 8/2013 Karlson
2013/0212234 A1 8/2013 Bartlett et al.
2013/0215475 A1 8/2013 Noguchi
2013/0238363 A1 9/2013 Ohta et al.
2013/0238968 A1 9/2013 Barrus
2013/0246384 A1 9/2013 Victor
2013/0262527 A1 10/2013 Hunter et al.
2013/0268331 A1 10/2013 Bitz et al.
2013/0297468 A1 11/2013 Hirsch et al.
2013/0307997 A1 11/2013 O'Keefe et al.
2013/0318424 A1 11/2013 Boyd
2013/0339051 A1 12/2013 Dobrean
2014/0002863 A1 1/2014 Hasegawa et al.
2014/0006326 A1 1/2014 Bazanov
2014/0012616 A1 1/2014 Moshenek
2014/0019842 A1 1/2014 Montagna et al.
2014/0033307 A1 1/2014 Schmidtler
2014/0043331 A1 2/2014 Makinen et al.
2014/0046638 A1 2/2014 Peloski
2014/0052749 A1 2/2014 Rissanen
2014/0058801 A1 2/2014 Deodhar et al.
2014/0059017 A1 2/2014 Chaney et al.
2014/0068403 A1 3/2014 Bhargav et al.
2014/0074545 A1 3/2014 Minder et al.
2014/0075301 A1 3/2014 Mihara
2014/0078557 A1 3/2014 Hasegawa et al.
2014/0082525 A1 3/2014 Kass et al.
2014/0095237 A1 4/2014 Ehrler et al.
2014/0101527 A1 4/2014 Suciu
2014/0108985 A1 4/2014 Scott et al.
2014/0109012 A1 4/2014 Choudhary et al.
2014/0111516 A1 4/2014 Hall et al.
2014/0115515 A1 4/2014 Adams et al.
2014/0115518 A1 4/2014 Abdukalykov et al.
2014/0129960 A1 5/2014 Wang et al.
2014/0136972 A1 5/2014 Rodgers et al.
2014/0137003 A1 5/2014 Peters et al.
2014/0137144 A1 5/2014 Jarvenpaa et al.
2014/0143252 A1 5/2014 Silverstein et al.
2014/0172475 A1 6/2014 Olliphant et al.
2014/0173401 A1 6/2014 Oshlag et al.
2014/0181155 A1 6/2014 Homsany
2014/0188748 A1 7/2014 Cavoue et al.
2014/0195933 A1 7/2014 Rao Dv
2014/0214404 A1 7/2014 Kalia et al.
2014/0215303 A1 7/2014 Grigorovitch et al.
2014/0229816 A1 8/2014 Yakub
2014/0240735 A1 8/2014 Salgado
2014/0249877 A1 9/2014 Hull et al.
2014/0257568 A1 9/2014 Czaja et al.
2014/0278638 A1 9/2014 Kreuzkamp et al.
2014/0278720 A1 9/2014 Taguchi
2014/0280287 A1 9/2014 Ganti et al.
2014/0280377 A1 9/2014 Frew
2014/0281868 A1 9/2014 Vogel et al.
2014/0281869 A1 9/2014 Yob
2014/0282417 A1 9/2014 Paveza et al.
2014/0289223 A1 9/2014 Colwell et al.
2014/0304174 A1 10/2014 Scott et al.
2014/0306837 A1 10/2014 Hauck
2014/0310345 A1 10/2014 Megiddo et al.
2014/0324497 A1 10/2014 Verma et al.
2014/0324501 A1 10/2014 Davidow et al.
2014/0325552 A1 10/2014 Evans et al.
2014/0359580 A1 12/2014 Boissy et al.
2014/0365938 A1 12/2014 Black et al.
2014/0372856 A1 12/2014 Radakovitz et al.
2014/0372932 A1 12/2014 Rutherford et al.
2015/0006205 A1* 1/2015 Chase .................... G06Q 40/08 705/4
2015/0032686 A1 1/2015 Kuchoor
2015/0033131 A1 1/2015 Peev et al.
2015/0033149 A1 1/2015 Kuchoor
2015/0035918 A1 2/2015 Matsumoto et al.
2015/0039387 A1 2/2015 Akahoshi et al.
2015/0046209 A1 2/2015 Choe
2015/0046900 A1 2/2015 Eldridge et al.
2015/0058619 A1 2/2015 Sweet et al.
2015/0067556 A1 3/2015 Tibrewal et al.
2015/0074721 A1 3/2015 Fishman et al.
2015/0074728 A1 3/2015 Chai et al.
2015/0088822 A1 3/2015 Raja et al.
2015/0095752 A1 4/2015 Studer et al.
2015/0100336 A1 4/2015 Ford et al.
2015/0106736 A1 4/2015 Torman et al.
2015/0125834 A1 5/2015 Mendoza Tascon
2015/0142676 A1 5/2015 Mcginnis et al.
2015/0142829 A1 5/2015 Lee et al.
2015/0153943 A1 6/2015 Wang
2015/0154660 A1 6/2015 Weald et al.
2015/0169514 A1 6/2015 Sah et al.
2015/0169531 A1 6/2015 Campbell et al.
2015/0178657 A1 6/2015 Kleehammer et al.
2015/0188964 A1 7/2015 Sharma et al.
2015/0205830 A1 7/2015 Bastide et al.
2015/0212717 A1 7/2015 Nair et al.
2015/0213397 A1 7/2015 Arena
2015/0220491 A1 8/2015 Cochrane et al.
2015/0234887 A1 8/2015 Greene et al.
2015/0242091 A1 8/2015 Lu et al.
2015/0248214 A1 9/2015 Gilger et al.
2015/0249864 A1 9/2015 Tang et al.
2015/0261796 A1 9/2015 Gould et al.
2015/0262121 A1 9/2015 Riel-Dalpe et al.
2015/0278699 A1 10/2015 Danielsson
2015/0281292 A1 10/2015 Kim et al.
2015/0295877 A1 10/2015 Roman et al.
2015/0310126 A1 10/2015 Steiner et al.
2015/0317590 A1 11/2015 Karlson
2015/0324453 A1 11/2015 Werner
2015/0331846 A1 11/2015 Guggilla et al.
2015/0363478 A1 12/2015 Haynes
2015/0370540 A1 12/2015 Coslovi et al.
2015/0370776 A1 12/2015 New
2015/0370904 A1 12/2015 Joshi et al.
2015/0378542 A1 12/2015 Saito et al.
2015/0378711 A1 12/2015 Cameron et al.
2015/0378979 A1 12/2015 Hirzel et al.
2015/0379472 A1 12/2015 Gilmour et al.
2016/0012111 A1 1/2016 Pattabhiraman et al.
2016/0018962 A1 1/2016 Low et al.
2016/0026939 A1 1/2016 Schiffer et al.
2016/0027076 A1 1/2016 Jackson et al.
2016/0035546 A1 2/2016 Platt et al.
2016/0041736 A1 2/2016 Schulz

(56) References Cited

U.S. PATENT DOCUMENTS

2016/0055134 A1 2/2016 Sathish et al.
2016/0055374 A1 2/2016 Zhang et al.
2016/0057163 A1 2/2016 Boffa et al.
2016/0063435 A1 3/2016 Shah et al.
2016/0068960 A1 3/2016 Jung et al.
2016/0078368 A1 3/2016 Kakhandiki et al.
2016/0088480 A1 3/2016 Chen et al.
2016/0092557 A1 3/2016 Stojanovic et al.
2016/0098574 A1 4/2016 Bargagni
2016/0117308 A1 4/2016 Haider et al.
2016/0170586 A1 6/2016 Gallo
2016/0173122 A1 6/2016 Akitomi et al.
2016/0196310 A1 7/2016 Dutta
2016/0210572 A1 7/2016 Shaaban et al.
2016/0216948 A1 7/2016 Mcpherson et al.
2016/0224532 A1 8/2016 Miller et al.
2016/0224676 A1 8/2016 Miller et al.
2016/0224939 A1 8/2016 Chen et al.
2016/0231915 A1 8/2016 Nhan et al.
2016/0232489 A1 8/2016 Skaaksrud
2016/0246490 A1 8/2016 Cabral
2016/0253982 A1 9/2016 Cheung et al.
2016/0259856 A1 9/2016 Ananthapur Bache et al.
2016/0275150 A1 9/2016 Bourbonnais et al.
2016/0292206 A1 10/2016 Ruiz Velazquez et al.
2016/0299655 A1 10/2016 Migos et al.
2016/0308963 A1 10/2016 Kung
2016/0321235 A1 11/2016 He et al.
2016/0321604 A1 11/2016 Imaeda et al.
2016/0335302 A1 11/2016 Wright et al.
2016/0335303 A1 11/2016 Madhalam et al.
2016/0335604 A1 11/2016 Reminick et al.
2016/0335731 A1 11/2016 Hall
2016/0335903 A1 11/2016 Mendoza Tascon
2016/0344828 A1 11/2016 Hausler et al.
2016/0350950 A1 12/2016 Ritchie et al.
2016/0381099 A1 12/2016 Keslin et al.
2017/0017779 A1 1/2017 Huang et al.
2017/0031967 A1 2/2017 Chavan et al.
2017/0038919 A1 2/2017 Moss et al.
2017/0041296 A1 2/2017 Ford et al.
2017/0052937 A1 2/2017 Sirven et al.
2017/0061342 A1 3/2017 Lore et al.
2017/0061360 A1 3/2017 Rucker et al.
2017/0061820 A1 3/2017 Firoozbakhsh
2017/0063722 A1 3/2017 Cropper et al.
2017/0075557 A1 3/2017 Noble et al.
2017/0076101 A1 3/2017 Kochhar et al.
2017/0090734 A1 3/2017 Fitzpatrick
2017/0090736 A1 3/2017 King et al.
2017/0091337 A1 3/2017 Patterson
2017/0093876 A1 3/2017 Feng et al.
2017/0097743 A1 4/2017 Hameed et al.
2017/0098001 A1* 4/2017 Yamamoto ......... G06Q 30/0631
2017/0109499 A1 4/2017 Doshi et al.
2017/0111327 A1 4/2017 Wu
2017/0116552 A1 4/2017 Deodhar et al.
2017/0124042 A1 5/2017 Campbell et al.
2017/0124048 A1 5/2017 Campbell et al.
2017/0124055 A1 5/2017 Radakovitz et al.
2017/0124740 A1 5/2017 Campbell et al.
2017/0126772 A1 5/2017 Campbell et al.
2017/0132296 A1 5/2017 Ding
2017/0132652 A1 5/2017 Kedzlie et al.
2017/0139874 A1 5/2017 Chin
2017/0139884 A1 5/2017 Bendig et al.
2017/0139891 A1 5/2017 Ah-Soon et al.
2017/0139992 A1 5/2017 Morin
2017/0140047 A1 5/2017 Bendig et al.
2017/0140219 A1 5/2017 King et al.
2017/0153771 A1 6/2017 Chu
2017/0161246 A1 6/2017 Klima
2017/0177556 A1 6/2017 Fay et al.
2017/0177888 A1 6/2017 Arora et al.
2017/0185575 A1 6/2017 Sood et al.
2017/0185592 A1 6/2017 Frei et al.
2017/0185668 A1 6/2017 Convertino et al.
2017/0200122 A1 7/2017 Edson et al.
2017/0201428 A1 7/2017 Normandin
2017/0206366 A1 7/2017 Fay et al.
2017/0212924 A1 7/2017 Semlani et al.
2017/0220813 A1 8/2017 Mullins et al.
2017/0221072 A1 8/2017 Athulurutlrumala et al.
2017/0228421 A1 8/2017 Sharma et al.
2017/0228445 A1 8/2017 Chiu et al.
2017/0228460 A1 8/2017 Amel et al.
2017/0229152 A1 8/2017 Loganathan et al.
2017/0236081 A1 8/2017 Grady Smith et al.
2017/0242921 A1 8/2017 Rota
2017/0257517 A1 9/2017 Panda
2017/0262786 A1 9/2017 Khasis
2017/0270970 A1 9/2017 Ho et al.
2017/0272316 A1 9/2017 Johnson et al.
2017/0272331 A1 9/2017 Lissack
2017/0277620 A1 9/2017 Kadioglu
2017/0277669 A1 9/2017 Sekharan
2017/0285879 A1 10/2017 Pilkington et al.
2017/0285890 A1 10/2017 Dolman
2017/0289619 A1 10/2017 Xu et al.
2017/0301039 A1 10/2017 Dyer et al.
2017/0315683 A1 11/2017 Boucher et al.
2017/0315714 A1 11/2017 Shyamsundar et al.
2017/0315974 A1 11/2017 Kong et al.
2017/0315979 A1 11/2017 Boucher et al.
2017/0316355 A1 11/2017 Shrestha et al.
2017/0322963 A1 11/2017 Ramamurthi et al.
2017/0324692 A1 11/2017 Zhou
2017/0329479 A1 11/2017 Rauschenbach et al.
2017/0351252 A1 12/2017 Kleifges et al.
2017/0351974 A1 12/2017 Rose et al.
2017/0372442 A1 12/2017 Mejias
2017/0374205 A1 12/2017 Panda
2018/0011827 A1 1/2018 Avery et al.
2018/0025084 A1 1/2018 Conlan et al.
2018/0026954 A1 1/2018 Toepke et al.
2018/0032492 A1 2/2018 Altshuller et al.
2018/0032570 A1 2/2018 Miller et al.
2018/0039651 A1 2/2018 Tobin et al.
2018/0055434 A1 3/2018 Cheung et al.
2018/0075104 A1 3/2018 Oberbreckling et al.
2018/0075115 A1 3/2018 Murray et al.
2018/0075413 A1 3/2018 Culver et al.
2018/0075560 A1 3/2018 Thukral et al.
2018/0081505 A1 3/2018 Ron et al.
2018/0081863 A1 3/2018 Bathla
2018/0081868 A1 3/2018 Willcock et al.
2018/0082072 A1 3/2018 Hosie et al.
2018/0088753 A1 3/2018 Viegas et al.
2018/0088989 A1 3/2018 Nield et al.
2018/0089299 A1 3/2018 Collins et al.
2018/0095938 A1 4/2018 Monte
2018/0096417 A1 4/2018 Cook et al.
2018/0109760 A1 4/2018 Metter et al.
2018/0121028 A1 5/2018 Kuscher et al.
2018/0121994 A1 5/2018 Matsunaga et al.
2018/0128636 A1 5/2018 Zhou
2018/0129651 A1 5/2018 Latvala et al.
2018/0157455 A1 6/2018 Troy et al.
2018/0157467 A1 6/2018 Stachura
2018/0157468 A1 6/2018 Stachura
2018/0157633 A1 6/2018 He et al.
2018/0173372 A1* 6/2018 Greenspan ............... G06N 3/09
2018/0173715 A1 6/2018 Dunne
2018/0174104 A1 6/2018 Schikora et al.
2018/0181650 A1 6/2018 Komatsuda et al.
2018/0181716 A1 6/2018 Mander et al.
2018/0189734 A1 7/2018 Newhouse et al.
2018/0210936 A1 7/2018 Reynolds et al.
2018/0225270 A1 8/2018 Bhide et al.
2018/0232422 A1 8/2018 Park et al.
2018/0260371 A1 9/2018 Theodore et al.
2018/0260435 A1 9/2018 Xu
2018/0262705 A1 9/2018 Park et al.
2018/0268337 A1 9/2018 Miller et al.

(56) References Cited

U.S. PATENT DOCUMENTS

2018/0276417 A1 9/2018 Cerezo Sanchez
2018/0285149 A1 10/2018 Bhandari et al.
2018/0285746 A1 10/2018 Dunwoody et al.
2018/0285756 A1 10/2018 Dunwoody et al.
2018/0285918 A1 10/2018 Staggs
2018/0293217 A1 10/2018 Callaghan
2018/0293587 A1 10/2018 Oda
2018/0293669 A1 10/2018 Jackson et al.
2018/0329930 A1 11/2018 Eberlein et al.
2018/0330320 A1 11/2018 Kohli
2018/0357047 A1 12/2018 Brown et al.
2018/0357305 A1 12/2018 Kinast et al.
2018/0364879 A1 12/2018 Adam et al.
2018/0365429 A1 12/2018 Segal
2018/0367484 A1 12/2018 Rodriguez et al.
2018/0373434 A1 12/2018 Switzer et al.
2018/0373757 A1 12/2018 Schukovets et al.
2019/0004773 A1 1/2019 Hoberman
2019/0005094 A1 1/2019 Yi et al.
2019/0011310 A1 1/2019 Turnbull et al.
2019/0012306 A1 1/2019 Dvorak
2019/0012342 A1 1/2019 Cohn
2019/0028360 A1 1/2019 Douglas et al.
2019/0034395 A1 1/2019 Curry et al.
2019/0036989 A1 1/2019 Eirinberg et al.
2019/0042628 A1 2/2019 Rajpara
2019/0050445 A1 2/2019 Griffith et al.
2019/0050466 A1 2/2019 Kim et al.
2019/0050812 A1 2/2019 Boileau
2019/0056856 A1 2/2019 Simmons et al.
2019/0065545 A1 2/2019 Hazel et al.
2019/0068703 A1 2/2019 Vora et al.
2019/0073350 A1 3/2019 Shiotani
2019/0079751 A1 3/2019 Foskett et al.
2019/0095413 A1 3/2019 Davis et al.
2019/0097909 A1 3/2019 Puri et al.
2019/0102425 A1 4/2019 Obeidat
2019/0108046 A1 4/2019 Spencer-Harper et al.
2019/0113935 A1 4/2019 Kuo et al.
2019/0114308 A1 4/2019 Hancock
2019/0114589 A1 4/2019 Voss et al.
2019/0123924 A1 4/2019 Embiricos et al.
2019/0130413 A1 5/2019 Nelson et al.
2019/0130611 A1 5/2019 Black et al.
2019/0138583 A1 5/2019 Silk et al.
2019/0138588 A1 5/2019 Silk et al.
2019/0138653 A1 5/2019 Roller et al.
2019/0147030 A1 5/2019 Stein et al.
2019/0155821 A1 5/2019 Dirisala
2019/0166110 A1 5/2019 Miu
2019/0179501 A1 6/2019 Seeley et al.
2019/0199823 A1 6/2019 Underwood et al.
2019/0208058 A1 7/2019 Dvorkin et al.
2019/0213557 A1 7/2019 Dotan-Cohen et al.
2019/0220161 A1 7/2019 Loftus et al.
2019/0236188 A1 8/2019 Mckenna
2019/0238636 A1 8/2019 Li et al.
2019/0243879 A1 8/2019 Harley et al.
2019/0251884 A1 8/2019 Burns et al.
2019/0258461 A1 8/2019 Li et al.
2019/0258706 A1 8/2019 Li et al.
2019/0286839 A1 9/2019 Mutha et al.
2019/0306009 A1 10/2019 Makovsky et al.
2019/0312899 A1 10/2019 Shulman et al.
2019/0324840 A1 10/2019 Malamut et al.
2019/0325012 A1 10/2019 Delaney et al.
2019/0327294 A1 10/2019 Subramani Nadar et al.
2019/0340550 A1 11/2019 Denger et al.
2019/0347077 A1 11/2019 Huebra
2019/0349447 A1 11/2019 Adams et al.
2019/0361879 A1 11/2019 Rogynskyy et al.
2019/0361971 A1 11/2019 Zenger et al.
2019/0364009 A1 11/2019 Joseph et al.
2019/0371442 A1 12/2019 Schoenberg
2019/0377791 A1 12/2019 Abou Mahmoud et al.
2019/0391707 A1 12/2019 Ristow et al.
2020/0005248 A1 1/2020 Gerzi et al.
2020/0005295 A1 1/2020 Murphy
2020/0012629 A1 1/2020 Lereya et al.
2020/0019548 A1 1/2020 Agnew et al.
2020/0019595 A1 1/2020 Azua Garcia
2020/0026352 A1 1/2020 Wang et al.
2020/0026397 A1 1/2020 Wohlstadter et al.
2020/0042648 A1 2/2020 Rao
2020/0050696 A1 2/2020 Mowatt et al.
2020/0053176 A1 2/2020 Jimenez Salgado et al.
2020/0117908 A1 4/2020 Pavetic et al.
2020/0125574 A1 4/2020 Ghoshal et al.
2020/0134002 A1 4/2020 Tung et al.
2020/0142546 A1 5/2020 Breedvelt-Schouten et al.
2020/0151630 A1 5/2020 Shakhnovich
2020/0159558 A1 5/2020 Bak et al.
2020/0175094 A1 6/2020 Palmer
2020/0176089 A1 6/2020 Jones et al.
2020/0192646 A1 6/2020 Yerramreddy et al.
2020/0192785 A1 6/2020 Chen
2020/0193388 A1 6/2020 Tran-Kiem et al.
2020/0236110 A1 7/2020 Metzler et al.
2020/0247661 A1 8/2020 Rao et al.
2020/0265112 A1 8/2020 Fox et al.
2020/0279315 A1 9/2020 Manggala
2020/0293337 A1 9/2020 Rangasamy et al.
2020/0293616 A1 9/2020 Nelson et al.
2020/0301678 A1 9/2020 Burman et al.
2020/0301902 A1 9/2020 Maloy et al.
2020/0310835 A1 10/2020 Momchilov
2020/0310888 A1 10/2020 Gopalan et al.
2020/0326824 A1 10/2020 Magahern et al.
2020/0327244 A1 10/2020 Blass et al.
2020/0334019 A1 10/2020 Bosworth et al.
2020/0348809 A1 11/2020 Drescher
2020/0349320 A1 11/2020 Owens
2020/0356740 A1 11/2020 Principato
2020/0356873 A1 11/2020 Nawrocke et al.
2020/0372055 A1 11/2020 Joko et al.
2020/0374146 A1 11/2020 Chhabra et al.
2020/0380212 A1 12/2020 Butler et al.
2020/0380449 A1 12/2020 Choi
2020/0387664 A1 12/2020 Kusumura et al.
2020/0401581 A1 12/2020 Eubank et al.
2020/0409949 A1 12/2020 Saxena et al.
2020/0410395 A1 12/2020 Ray et al.
2021/0014136 A1 1/2021 Rath
2021/0019287 A1 1/2021 Prasad et al.
2021/0021603 A1 1/2021 Gibbons
2021/0026598 A1 1/2021 Zinsmeyer et al.
2021/0034058 A1 2/2021 Subramanian et al.
2021/0034443 A1 2/2021 Lowin et al.
2021/0035069 A1 2/2021 Parikh
2021/0042796 A1 2/2021 Khoury et al.
2021/0049524 A1 2/2021 Nachum et al.
2021/0049555 A1 2/2021 Shor
2021/0055955 A1 2/2021 Yankelevich et al.
2021/0056509 A1 2/2021 Lindy
2021/0065203 A1 3/2021 Billigmeier et al.
2021/0072883 A1 3/2021 Migunova et al.
2021/0073526 A1 3/2021 Zeng et al.
2021/0075870 A1 3/2021 Kempf et al.
2021/0081404 A1 3/2021 Kempf et al.
2021/0084120 A1 3/2021 Fisher et al.
2021/0096852 A1 4/2021 Stump et al.
2021/0117864 A1 4/2021 Weast et al.
2021/0124749 A1 4/2021 Suzuki et al.
2021/0124872 A1 4/2021 Lereya
2021/0136027 A1 5/2021 Barbitta et al.
2021/0141923 A1 5/2021 Wu et al.
2021/0149553 A1 5/2021 Lereya et al.
2021/0149688 A1 5/2021 Newell et al.
2021/0149925 A1 5/2021 Mann et al.
2021/0150489 A1 5/2021 Haramati et al.
2021/0158214 A1 5/2021 Witt et al.
2021/0165782 A1 6/2021 Deshpande et al.
2021/0166196 A1 6/2021 Lereya et al.
2021/0166339 A1 6/2021 Mann et al.

(56) References Cited

U.S. PATENT DOCUMENTS

2021/0173682 A1 6/2021 Chakraborti et al.
2021/0174006 A1 6/2021 Stokes
2021/0192126 A1 6/2021 Gehrmann et al.
2021/0203549 A1 7/2021 Snehashis et al.
2021/0232484 A1 7/2021 Keneally et al.
2021/0248311 A1 8/2021 Helft et al.
2021/0257065 A1 8/2021 Mander et al.
2021/0264220 A1 8/2021 Wei et al.
2021/0271726 A1 9/2021 Trainor
2021/0273957 A1 9/2021 Boyer et al.
2021/0281428 A1 9/2021 Kempf et al.
2021/0304020 A1 9/2021 Kaplan
2021/0326519 A1 10/2021 Lin et al.
2021/0328888 A1 10/2021 Rath
2021/0342145 A1 11/2021 Miller et al.
2021/0342785 A1 11/2021 Mann et al.
2021/0357579 A1 11/2021 Lereya et al.
2021/0365446 A1 11/2021 Srivastava et al.
2021/0374197 A1 12/2021 Chauhan
2021/0382611 A1 12/2021 Gan
2021/0397585 A1 12/2021 Seward
2022/0011732 A1 1/2022 Hall
2022/0066847 A1 3/2022 Liu et al.
2022/0099454 A1 3/2022 Decrop et al.
2022/0103589 A1 3/2022 Shen et al.
2022/0121325 A1 4/2022 Roberts et al.
2022/0121478 A1 4/2022 Chivukula et al.
2022/0129283 A1 4/2022 Sharma et al.
2022/0138004 A1 5/2022 Nandakumar et al.
2022/0147934 A1 5/2022 Chandrashekar et al.
2022/0191251 A1 6/2022 Gavish et al.
2022/0206864 A1 6/2022 Nadathur et al.
2022/0221591 A1 7/2022 Smith et al.
2022/0222427 A1 7/2022 Mann et al.
2022/0229928 A1 7/2022 Shachar et al.
2022/0237550 A1 7/2022 Jennings et al.
2022/0245328 A1 8/2022 Tsabba
2022/0261288 A1 8/2022 Viswanathan et al.
2022/0291666 A1 9/2022 Cella et al.
2022/0292180 A1 9/2022 Chauhan
2022/0300850 A1 9/2022 Mendez et al.
2022/0308918 A1 9/2022 Pandey et al.
2022/0335362 A1 10/2022 Nikain et al.
2022/0343258 A1 10/2022 Wilde et al.
2022/0351564 A1 11/2022 Sahani et al.
2022/0357905 A1 11/2022 Dohmae
2022/0358190 A1 11/2022 Baghani et al.
2022/0375145 A1 11/2022 Herath et al.
2022/0382522 A1 12/2022 Heynemann Nascentes Da Silva et al.
2022/0413846 A1 12/2022 Clarke et al.
2023/0004832 A1 1/2023 Sahasi et al.
2023/0004900 A1 1/2023 Gleave
2023/0014233 A1 1/2023 Xiang et al.
2023/0016946 A1 1/2023 Wouhaybi et al.
2023/0035600 A1 2/2023 Holzman et al.
2023/0075183 A1 3/2023 Copty et al.
2023/0081880 A1 3/2023 Mathur et al.
2023/0083891 A1 3/2023 Achin et al.
2023/0093470 A1 3/2023 Dvornik et al.
2023/0107316 A1 4/2023 Ripa et al.
2023/0108808 A1 4/2023 Lerman
2023/0113369 A1 4/2023 Wang et al.
2023/0142774 A1 5/2023 Hashemi et al.
2023/0153651 A1 5/2023 Bi et al.
2023/0153724 A1 5/2023 Thampy et al.
2023/0171241 A1 6/2023 Amichay et al.
2023/0188516 A1 6/2023 Danilov et al.
2023/0230006 A1 7/2023 Bosch et al.
2023/0259390 A1 8/2023 Howley et al.
2023/0259839 A1 8/2023 Manalo et al.
2023/0281040 A1 9/2023 Cao
2023/0316382 A1 10/2023 Faricy et al.
2023/0385085 A1 11/2023 Singh
2023/0393832 A1 12/2023 Touati et al.
2023/0396641 A1 12/2023 Hebbagodi et al.
2023/0419161 A1 12/2023 Dines
2024/0046142 A1 2/2024 Marks et al.
2024/0053727 A1 2/2024 Timisescu et al.
2024/0054526 A1 2/2024 Horwitz et al.
2024/0078724 A1 3/2024 Brehmer et al.
2024/0169519 A1 5/2024 Tjon
2024/0250977 A1 7/2024 Shulman et al.
2024/0283759 A1 8/2024 Adams
2024/0345807 A1 10/2024 Duggal et al.
2024/0361995 A1 10/2024 Somasundaram et al.

FOREIGN PATENT DOCUMENTS

CN 107123424 A 9/2017
CN 107422666 A 12/2017
CN 107623596 A 1/2018
CN 107885656 A 4/2018
CN 108717428 A 10/2018
CN 112929172 A 6/2021
DE 102013104892 A1 11/2014
EP 3443466 B1 12/2021
JP H0756821 A 3/1995
KR 1020150100760 A 9/2015
KR 1020220016276 A 2/2022
WO 2004100015 A2 11/2004
WO 2006116580 A2 11/2006
WO 2008109541 A1 9/2008
WO 2014088393 A1 6/2014
WO 2017202159 A1 11/2017
WO 2018023798 A1 2/2018
WO 2018042424 A1 3/2018
WO 2020139865 A1 7/2020
WO 2020187408 A1 9/2020
WO 2020215123 A1 10/2020
WO 2021096944 A1 5/2021
WO 2021144656 A1 7/2021
WO 2021161104 A1 8/2021
WO 2021183312 A1 9/2021
WO 2021220058 A1 11/2021
WO 2022153122 A1 7/2022
WO 2023186048 A1 10/2023

OTHER PUBLICATIONS

List of IBM Patents or Patent Applications Treated as Related, Apr. 21, 2021, 2 pages.

Abor Jr. C., “Low-Code and No-Code AI: New AI Development—What is code anymore?!?!” Linkedin, Published Jul. 15, 2023, Retrieved from <https://www.linkedin.com/pulse/ low-code-no-code-ai-new-development-what-code-anymore-c-l-abor-jr>, 15 pages.

Anupam et al., “Personalizing the Web Using Site Descriptions,” In: Proceedings of the Tenth International Workshop on Database and Expert Systems Applications, Sep. 1999, 7 pages.

Aylward, Grant, “Drag-and-Drop AI Enables Digital Workforce Deployment at Scale Share,” Blue Prism, Mar. 19, 2020, Retrieved from <https://www.blueprism.com/resources/ blog/drag-and-drop-ai-enables-digital-workforce-deployment-at-scale/>, 10 pages.

Baarslag et al., “Negotiation as an Interaction Mechanism for Deciding App Permissions,” In: Proceedings of the 2016 CHI Conference Extended Abstracts on Human Factors in Computing Systems, 2016, pp. 2012-2019.

Bahrebar et al., “A Novel Type-2 Fuzzy Logic for Improved Risk Analysis of Proton Exchange Membrane Fuel Cells in Marine Power Systems Application,” Energies, Mar. 22, 2018, vol. 11, No. 721, pp. 1-16.

Barai et al., “Image Annotation System Using Visual and Textual Features,” In: Proceedings of the 16th International Conference on Distributed Multi-media Systems, 2010, 8 pages.

Basic Walkthrough, Aug. 9, 2019, Retrieved from <https://www.youtube.com/watch?v=VpbgWyPf74g>, 16 pages.

Breitgand et al., “Serverless Data Analytics Platform: D3.1 Intital specs of the Serverless Compute and Execution Engine,” CloudButton, Jul. 22, 2019, Retrieved from <https://cloudbutton.eu/docs/deliverables/CloudButton_D3.1_Public.pdf>, 56 pages.

(56) References Cited

OTHER PUBLICATIONS

Chen et al., "Artificial Intelligence in Education: A Review," IEEEAccess, Apr. 2020, vol. 8, pp. 75264-75278.
Demonstracion en espanol de Monday.com, Published Feb. 20, 2019, Retrieved from <https://www.youtube.com/watch?v=zOqydTgof1A>, 53 pages.
Desmedt et al., "Function-Based Access Control (FBAC) From Access Control Matrix to Access Control Tensor," In: Proceedings of the 8th ACM CCS International Workshop on Managing Insider Security Threats, 2016, 12 pages.
Donath, Judith, "Interfaces Make Meaning," Chapter 3 from the Social Machine: Designs for Living Online, 2014, pp. 41-76.
Dorn et al., "Efficient Full-Field Vibration Measurements and Operational Modal Analysis Using Neuromorphic Event-Based Imaging," Journal of Engineering Mechanics, Jul. 1, 2018, vol. 144, No. 7, 25 pages.
Features, daPulse, Nov. 2021, Retrieved from <web.archive.org/web/20140918184 21/https://dapulse.com/features>, 22 pages.
Freund, Karl, "SiMa.ai Creates Drag-And-Drop Platform for Building AI Workflows," Forbes, Sep. 12, 2023, Retrieved from <https://www.forbes.com/sites/karlfreund/2023/09/12/simaai-creates-drag-and-drop-platform-for-building-ai-workflows/?sh=789de8466046>, 6 pages.
Gutwin et al., "Supporting Informal Collaboration in Shared-Workspace Groupware," Journal of Universal Computer Science, 2008, vol. 14, No. 9, pp. 1411-1434.
High Level Overview, daPulse, 2016, Retrieved from <https://web.archive.org/web/20161104170936/https://dapulse.com>, 12 pages.
Hupfer et al., "Introducing collaboration into an application development environment," In: Proceedings of the 2004 ACM Conference on Computer Supported Cooperative Work, Nov. 2004, vol. 6, No. 3, pp. 21-24.
International Search Report and Written Opinion in PCT/IB2020/000024, mailed Jun. 9, 2020, 10 pages.
International Search Report and Written Opinion in PCT/IB2020/000658, mailed Nov. 11, 2020, 8 pages.
International Search Report and Written Opinion in PCT/IB2020/000974, mailed May 3, 2021, 15 pages.
International Search Report and Written Opinion in PCT/IB2021/000090, mailed Jul 27, 2021, 12 pages.
International Search Report and Written Opinion in PCT/IB2021/000297, mailed Oct. 12, 2021, 17 pages.
International Search Report and Written Opinion in PCT/IB2023/061991, mailed Feb. 26, 2024, 6 pages.
International Search Report and Written Opinion in PCT/IB2023/061992, mailed Mar. 19, 2024, 7 pages.
International Search Report and Written Opinion in PCT/IB2023/061994, mailed Apr. 25, 2024, 11 pages.
International Search Report and Written Opinion in PCT/IB2024/055803, mailed Sep. 30, 2024, 13 pages.
Ionescu et al., "A chat-centric collaborative environment for web-based real-time collaboration," 2015 IEEE 10th Jubilee International Symposium on Applied Computational Intelligence and Informatics, May 21-23, 2015, pp. 105-110.
Kantorovitz, Isaiah, "Lexical Analysis Tool," May 2004, Retrieved from <https://dl.acm.org/doi/pdf/10.1145/997140.997147>, vol. 39, No. 5, pp. 66-74.
Kollmann, Franz, "Realizing Fine-Granular Read and Write Rights on Tree Structured Documents," in: The Second International Conference on Availability, Reliability and Security, 2007, 7 pages.
Larson, Stephen, "Introducing Data Mining Concepts Using Microsoft Excel's Table Analysis Tools," Oct. 2015, Retrieved from <https://dl.acm.org/doi/pdf/10.5555/2831373.2831394>, pp. 127-129.
Lins et al., "Artificial Intelligence as a Service," Business & Information Systems Engineering, vol. 63, 2021, pp. 441-456.
List et al., "An Evaluation of Conceptual Business Process Modelling Languages," In: Proceedings of the 2006 ACM symposium on Applied Computing, Apr. 2006, pp. 1532-1539.
Monday.com Walkthrough 2018/All Features, Platforms & Thoughts, Transcription Provided, Mar. 1, 2018, pp. 1-55.
Ni et al., "Asynchronous Event-Based Visual Shape Tracking for Stable Haptic Feedback in Microrobotics," IEEE Transactions on Robotics, vol. 28, No. 5, Oct. 1, 2012, pp. 1081-1089.
Oey et al. "Developing integrated performance dashboards with Power BI—a case study in a medium-size Manufacturer." 2021 International Conference on Information Management and Technology (ICIMTech). vol. 1. IEEE, (2021): 265-270.
Pedersen et al., "Tivoli: an electronic whiteboard for informal workgroup meetings," Conference on Human Factors in Computing Systems: Proceedings of the Interact '93 and CHI '93 conference on Human factors in computing systems, Apr. 24-29, 1993, pp. 391-398.
Peltier, J., "Clustered and Stacked Column and Bar Charts," Peltier Technical Services, Inc., Aug. 2011, 128 pages.
Pivot table, Wikipedia, Jul. 2021, Retrieved from <https://en.wikepedia .org/w/index.php?title=Pivottable&oldid=857163289>, 5 pages.
Rodrigo, A., "Project Management with Monday.com: A 101 Introduction," Envato Tuts+, Jul. 22, 2019, Retrieved from <https://business.tutsplus.com/tutorials/project-management-with-mondaycom--cms-33586>, 11 pages.
Singh et al., "A Theoretical Framework of a BIM-based Multi-Disciplinary Collaboration Platform," Automation in Construction, Nov. 2011, vol. 20, pp. 134-144.
Sreenath et al., "Agent-based service selection," Journal of Web Semantics 1.3, Oct. 2003, 29 pages.
Stancu et al., "SecCollab-Improving Confidentiality for Existing Cloud-Based Collaborative Editors," In: 2017 21st International Conferences on Control Systems and Computer Science, 2017, pp. 324-331.
Stohr, E., "Workflow Automation: Overview and Research Issues," Information Systems Frontiers, 2001, pp. 281-296.
Sun et al., "Geoweaver: Advanced Cyberinfrastructure for Managing Hybrid Geoscientific AI Workflows," International Journal of Geo-Information, Feb. 2020, vol. 9, 20 pages.
Switch Presenter While Using ShowMyPC, ShowMyPC, Aug. 2016, Retrieved from <The Wayback Machine>, 1 page.
Using Filters in Overview, Published Mar. 7, 2017, Retrieved from <https://www.youtube.com/watch?v=hycANhz7gww> 1 page.
Veenendaal, A. "How to Use Generative AI for Document Extraction & Processing." SS&C Blue Prism. (2023):1-8.
Wilson et al., "Beyond Social Graphs: User Interactions in Online Social Networks and their Implications," ACM Transactions on the Web, Nov. 2012, vol. 6, No. 4, 31 pages.
Yamada et al., "A Software Tag Generation System to Realize Software Traceability," 2010 Asia Pacific Software Engineering Conference, pp. 423-432.
Zhang et al. "Artificial intelligence in recommender systems." Complex & intelligent systems 7.1 (2021): 439-457.
Zhang et al., "Integrating semantic NLP and logic reasoning into a unified system for fully-automated code checking," Automation in Construction, 2017, vol. 73, 2017, pp. 45-57.

* cited by examiner

Figure 3A:
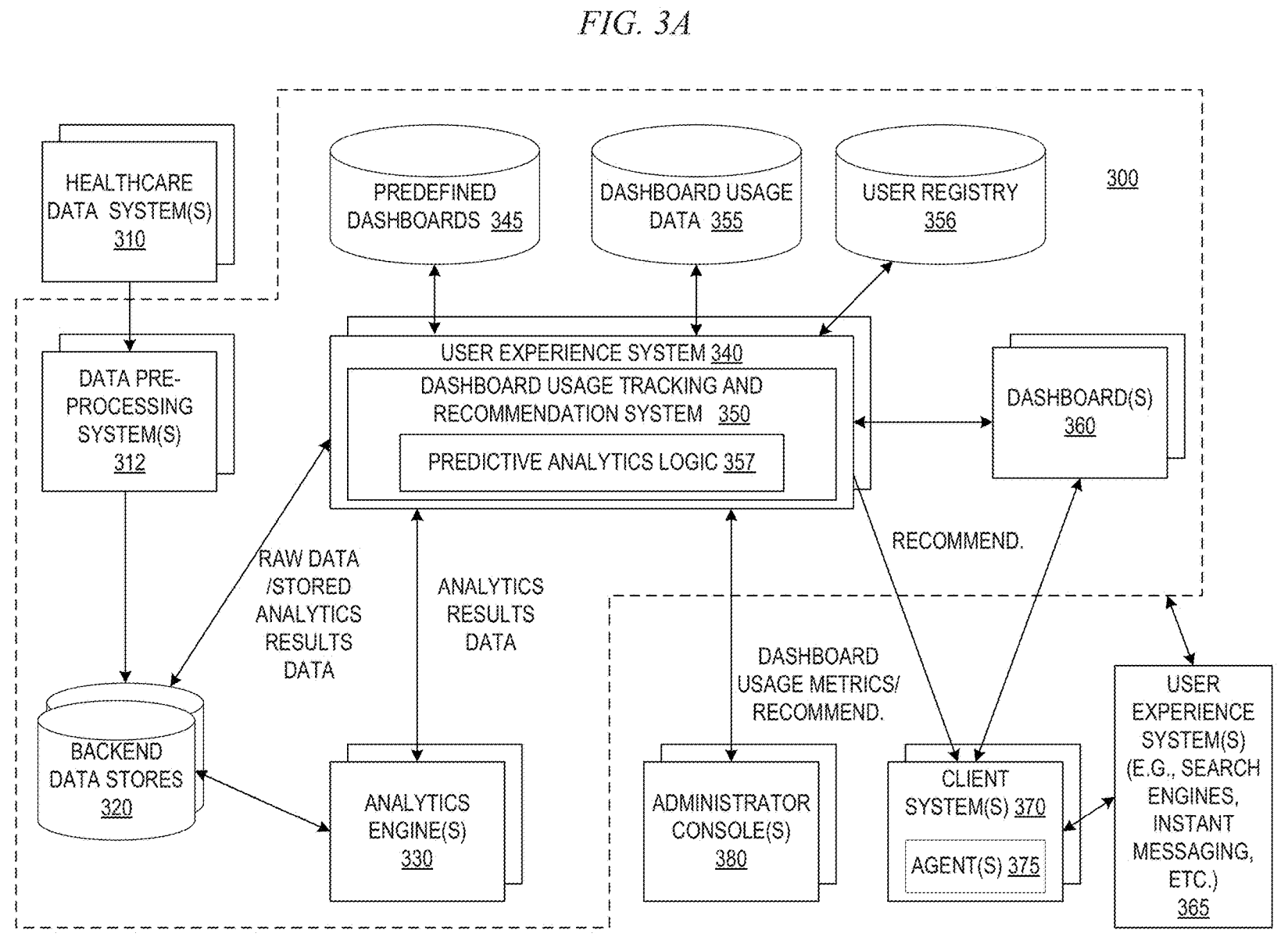

HEALTHCARE DATA SYSTEM(S) 310

DATA PRE-PROCESSING SYSTEM(S) 312

BACKEND DATA STORES 320

PREDEFINED DASHBOARDS 345

DASHBOARD USAGE DATA 355

USER REGISTRY 356

USER EXPERIENCE SYSTEM 340

DASHBOARD USAGE TRACKING AND RECOMMENDATION SYSTEM 350

PREDICTIVE ANALYTICS LOGIC 357

DASHBOARD(S) 360

RAW DATA /STORED ANALYTICS RESULTS DATA

ANALYTICS RESULTS DATA

DASHBOARD USAGE METRICS/ RECOMMEND.

RECOMMEND.

ANALYTICS ENGINE(S) 330

ADMINISTRATOR CONSOLE(S) 380

CLIENT SYSTEM(S) 370

AGENT(S) 375

USER EXPERIENCE SYSTEM(S) (E.G., SEARCH ENGINES, INSTANT MESSAGING, ETC.) 365

DASHBOARD USAGE TRACKING AND GENERATION OF DASHBOARD RECOMMENDATIONS

BACKGROUND

The present application relates generally to an improved data processing apparatus and method and more specifically to mechanisms for tracking dashboard usage and generating recommendations as to dashboards or portions of dashboards that may be of interest based on analysis of such usage.

In information technology, a dashboard is a user interface that organizes and presents information that is easy for users to view and interact with. The user interface is referred to as a "dashboard" since it resembles an automobile dashboard in that it typically has a variety of different information presented in different formats within the same overall visualization. However, a computing environment dashboard is more likely to be interactive than an automobile dashboard and provides user interface elements, such as virtual buttons, drop-down menus, and other generally known user interface mechanisms for receiving user input, through which the user can interact with the visualization in order to access detailed information.

Dashboard user interfaces have been utilized in various industries to present information to users in an interactive manner such that the user may drill down into the underlying analytics supporting the visualizations presented in the dashboard. Recently, dashboards have been utilized in the healthcare industry to present various levels of information to users within an organization. For example, Truven Health Analytics, an International Business Machines Corporation (IBM) company, has provided a variety of computer based solutions for providing health analytics and corresponding dashboards for presenting the resulting information to users.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a data processing system comprises at least one memory and at least one processor, where the at least one memory comprises instructions that are executed by the at least one processor to configure the at least one processor to implement a method. The method comprises presenting, by the data processing system, a dashboard interface to a user via a client computing device, and tracking, by the data processing system, user inputs to the client computing device at least during and after presentation of the dashboard interface to the user via the client computing device. The method further comprises applying, by the data processing system, predictive analytics to the tracked user inputs to predict a type of data the user is attempting to access, and correlating, by the data processing system, the predicted type of data with one or more portions of one or more other dashboard interfaces that provide a representation of data having a type matching the predicted type of data. Furthermore, the method comprises outputting, by the data processing system, a recommendation output to the user via the client computing device recommending the user access the one or more other dashboard interfaces.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

The invention, as well as a preferred mode of use and further objectives and advantages thereof, will best be understood by reference to the following detailed description of illustrative embodiments when read in conjunction with the accompanying drawings, wherein:

FIG. 3A is an example block diagram of the primary operational elements of a dashboard usage tracking and recommendation system in accordance with one illustrative embodiment;

Figure 5:
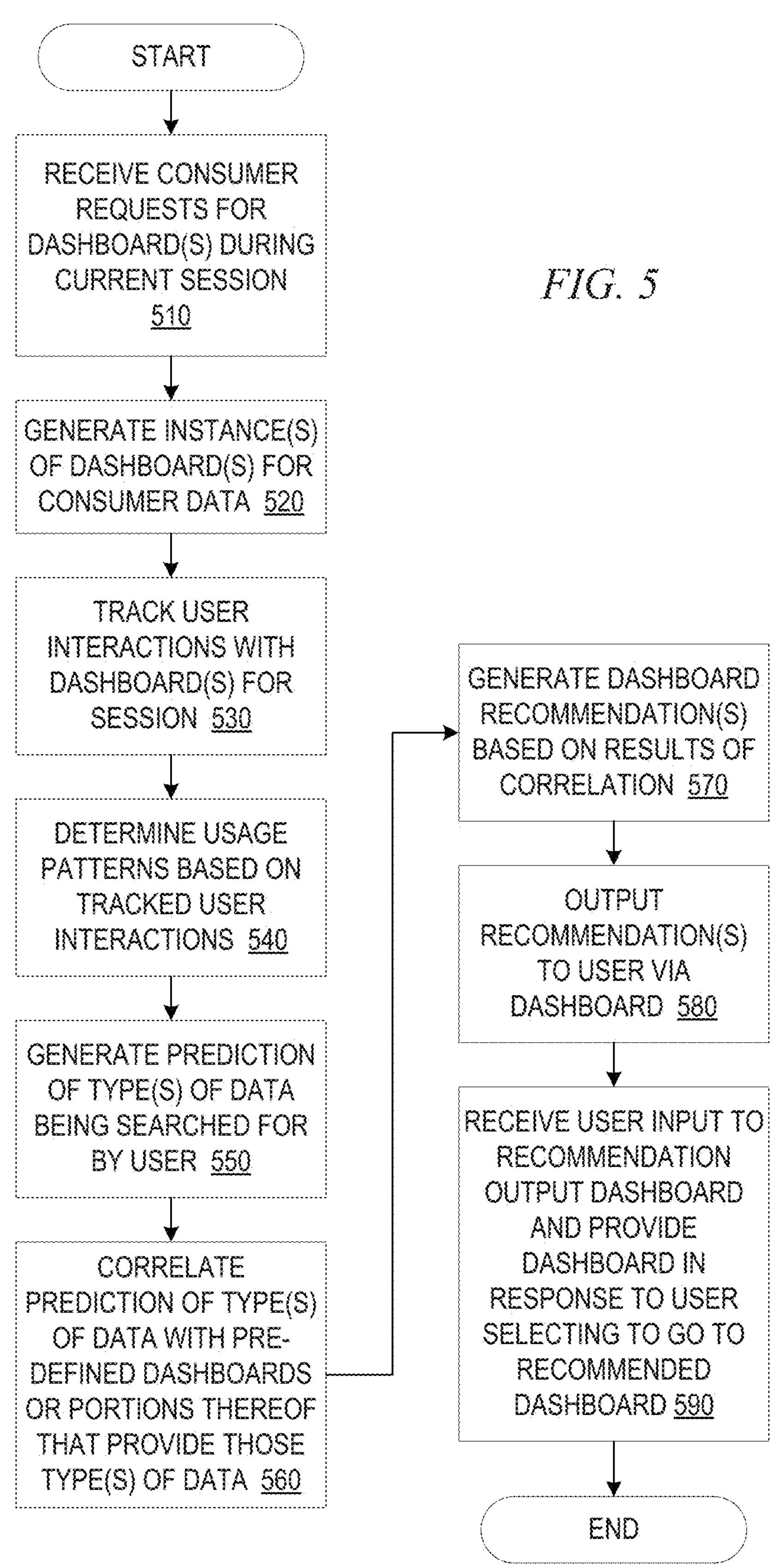
Figure 6:
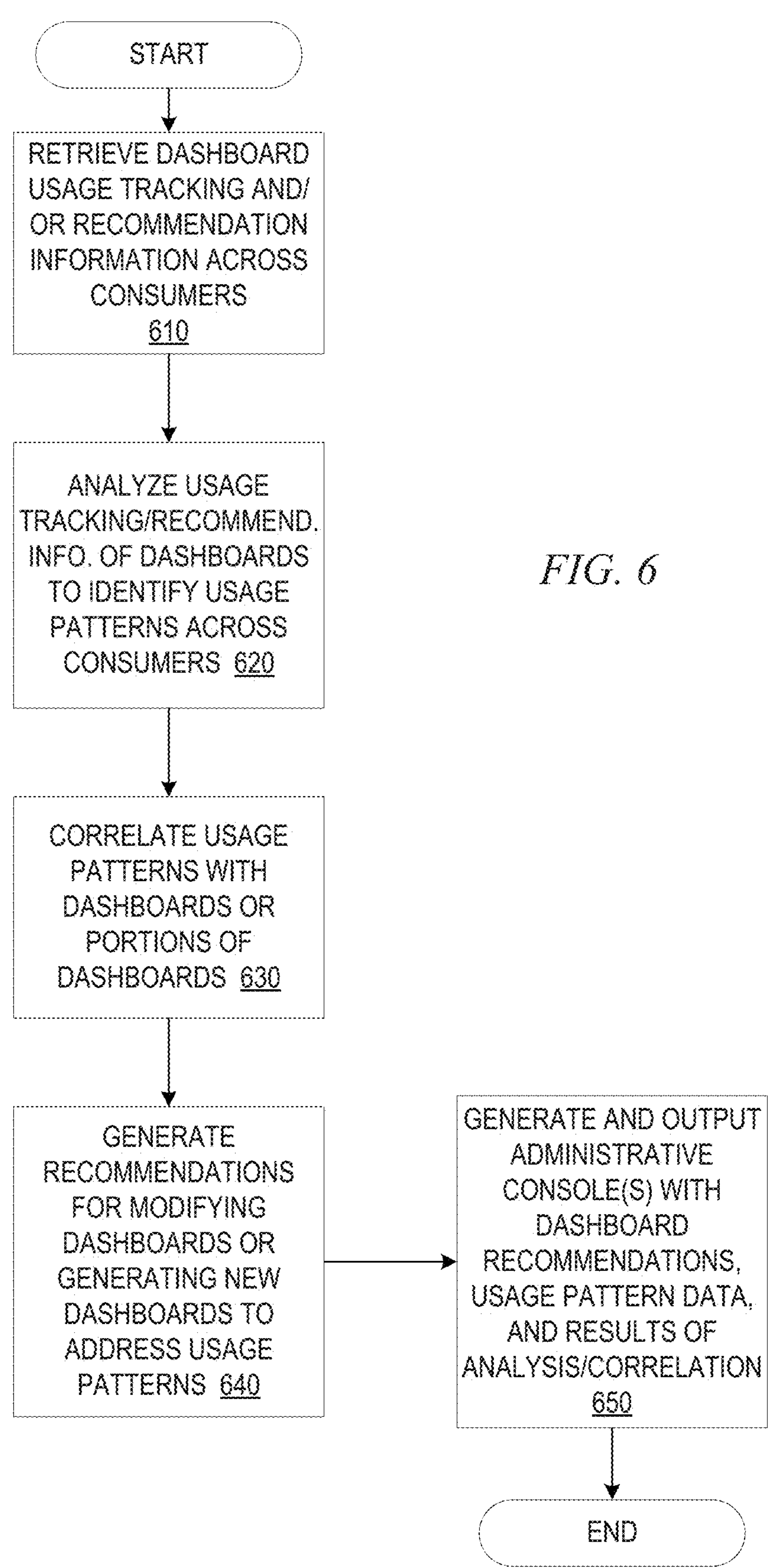

FIG. 5 is a flowchart outlining an example operation for providing a dashboard recommendation to a user based on dashboard tracking and analysis in accordance with one illustrative embodiment; and FIG. 6 is a flowchart outlining an example operation for generating administrative consoles for providing dashboard recommendations across multiple users and/or organizations in accordance with one illustrative embodiment.

The illustrative embodiments provide mechanisms for tracking dashboard usage and generating recommendations as to dashboards or portions of dashboards that may be of interest based on analysis of such usage. The mechanisms of the illustrative embodiments track usage patterns of dashboards and predict the information that a user is attempting to obtain, correlates this information with dashboard configuration information specifying the information that various dashboards provide, and selects one or more dashboards that provide information corresponding to the predicted information for recommending to the user. In addition, the mechanisms of the illustrative embodiments analyze usage patterns across multiple users and/or organizations to determine the ways in which organizations and users within organizations are using various dashboards and generates recommendations with regard to the various dashboards.

In particular, it has been recognized that while dashboards provide a useful tool to present a variety of information to a user via one overall visualization of a general category of information, many times users must hunt for and utilize multiple different dashboards to obtain the particular information, or combination of information, that the user wishes to view. This stems from the fact that dashboards are pre-defined and dashboard creators, when generating a dashboard definition, must predict what information users are most likely going to want to view when requesting a particular dashboard, e.g., a dashboard creator that is generating a "Health Plan Dashboard" may determine that users are most likely going to want to view claims cost per member information, trend rates information, patient demographic information, high cost claimant (HCC) information, and the like.

However, many times users wish to see different combinations of information or utilize a dashboard expecting certain information to be present in the dashboard but which the creator did not predict the user would expect to be present in the dashboard. Thus, as a result, users often may not obtain the information that they are looking for from a single dashboard and may have to hunt for the information in other dashboards. In cases where users are not aware of the content of various dashboards or are not aware of what dashboards provide the information that they seek, the user may navigate many different dashboards and still not arrive at the desired information. This can cause frustration on the part of the user and may affect the efficiency or accuracy by which a user is able to perform assigned tasks. Moreover, organizations whose users are utilizing these dashboards or which are responsible for providing such dashboards may wish to know when users are not obtaining the information that they seek or otherwise know where improvements in the dashboard offerings may be achieved.

The illustrative embodiments provide mechanisms to track and analyze user interactions with dashboards, as well as their actions before and/or after interacting with the dashboard, e.g., searches performed via search engines, other dashboards accessed, instant messages sent, etc., to determine the information that a user is attempting to obtain through use of the dashboard and to determine whether the dashboard provided the information. Moreover, other usage tracking information, such as an amount of time spent accessing a dashboard, the portions of the dashboard interacted with by the user, and the like, may be tracked to give an indication of the usability of the dashboard and the type of information the user appears to be attempting to access. A pattern of usage, or dashboard user behavior, is generated based on the tracking and analysis and used to determine commonalities and differences between the dashboards accessed, the keywords searched, keywords included in instant messages, and the like. Based on this pattern of usage information, a determination is made, using predictive analytics, as to the information that the user is most likely attempting to access. Based on the determination of the information that the user is most likely attempting to access, the mechanisms of the illustrative embodiments perform a search of dashboard characteristic data to identify one or more dashboards, if any, that provide the information that the user appears to be searching for.

A recommendation may then be output to the user via a portion of a dashboard, a separate dialog box, or any other suitable output mechanism, that indicates what information the illustrative embodiments believe the user is looking for and the one or more dashboards that provide that information. This output may further provide links or other user interface elements by which the user may select the dashboard that the user would like to access and thereby be redirected to the recommended dashboard. Moreover, in some illustrative embodiments, characteristics of other users that accessed the same dashboard, as well as their usage information with regard to other dashboards, recommendations provided to these other users, and the like, may be leveraged to determine a recommendation as to other dashboards that the user may wish to access.

In addition, the mechanisms of the illustrative embodiments may log or otherwise store historical information about user usage patterns, as well as any recommended dashboards that the user actually selected based on the providing of the recommendation output to the user, for usage tracking and analysis across a plurality of users of the same and/or different organizations. For example, usage tracking and analysis information may identify commonalities between users that use a particular dashboard as to other dashboards accessed thereafter within a same user session, commonalities of search terms used in search queries after accessing the dashboard, commonalities of keywords included in instant messages sent after accessing a dashboard, or the like, which all point to users not obtaining the information they seek from the accessed dashboard and a commonality in the information that these users thought would be available in the dashboard. This provides insight into ways in which the accessed dashboard may be improved, a new dashboard that may be of use to users, or other modifications to the set of dashboards that are made available to users at the various organizations.

As mentioned above, the dashboard usage tracking and analysis may be done across organizations such that organizations whose users are attempting to access similar types of information from their dashboards, or are using similar dashboards in similar ways, may be identified and recommendations provided based on what other similar organizations' users are doing to access similar information or recommendations that have been provided to other similar organizations. In such cases, information about the various organizations may be utilized to identify similar organizations and identify similarities in usage patterns of their users with regard to similar dashboards.

For example, a dashboard provider may provide the same or similar dashboards to multiple organizations. These organizations may customize these dashboards for their own personal use and may use them to access their own personal backend data stores. Tracking and analysis of usage patterns of users of the various organizations may provide insights into recommendations for how to modify, or add to, the dashboard offerings for a particular organization. In addition, looking at usage patterns across multiple similar organizations may identify areas where the dashboard offerings are not meeting the information needs of users in general, regardless of the particular organization, and provide insights into how all dashboard offerings to all organizations may be improved. Moreover, such across organization analysis may allow recommendations for one organization to influence recommendations provided to another organization based on similarities of usage patterns of their users and similarities of organization characteristics, e.g., organization size, geography, business segment, level of analytics utilized, etc.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java™ Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for tracking dashboard usage and generating recommendations as to dashboards or portions of dashboards that may be of interest based on analysis of such usage. It should be appreciated that the mechanisms of the illustrative embodiments may be utilized to track dashboard usage patterns and analyze such patterns to provide dashboard recommendations in many different domains. For example, one domain that will be referenced in the examples provided herein is the healthcare domain in which healthcare data may be obtained from various sources, e.g., hospitals, doctor offices, health insurance providers, and the like, pre-processed to take the raw data and place the raw data into a form that is useable by analytics engines, stored in a backend store, and upon which healthcare analytics are executed by the analytics engines to generate analytical and statistical data that may be used as a basis for generating one or more dashboard representations. While this is an example implementation that will be used to provide examples herein, it should be appreciated that the present invention is not limited to such. Rather, the mechanisms of the illustrative embodiments may be utilized in any domain where dashboards are utilized by users to obtain information representations. This may include many different types of business, governmental, and other organization domains.

Figure 1:
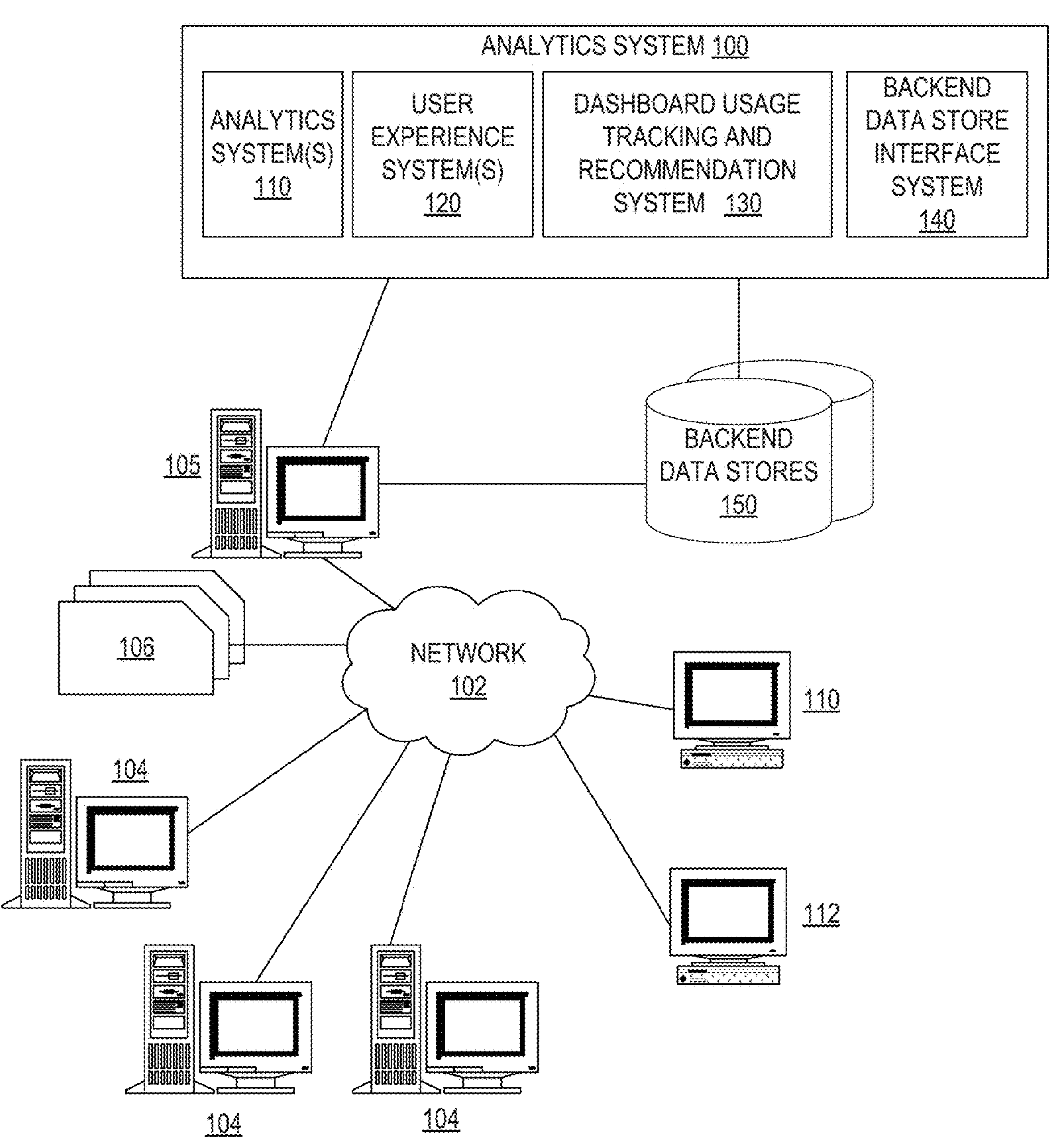
FIG. 1 depicts a schematic diagram of one illustrative embodiment of an analytics system implanting a dashboard usage tracking and recommendation system in accordance with one illustrative embodiment.
Figure 2:
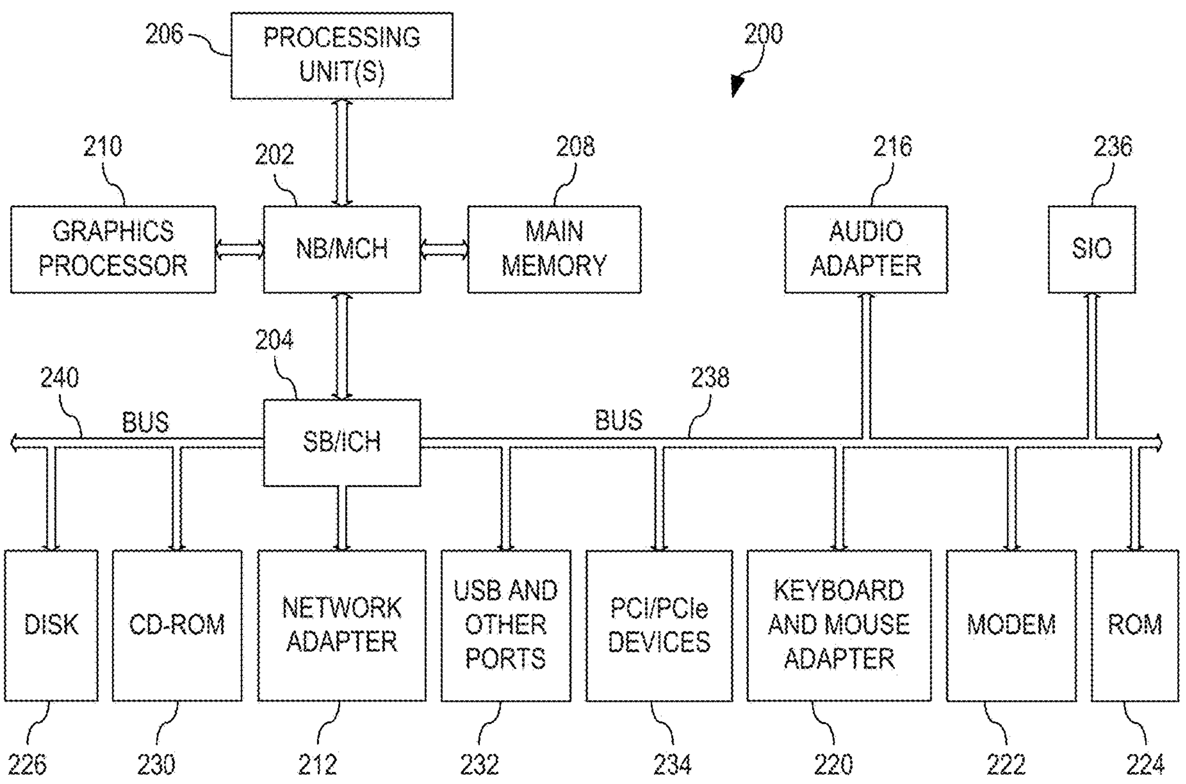
FIG. 2 is a block diagram of an example data processing system in which aspects of the illustrative embodiments are implemented.

The illustrative embodiments may be utilized in many different types of data processing environments. In order to provide a context for the description of the specific elements and functionality of the illustrative embodiments, FIGS. 1-2 are provided hereafter as example environments in which aspects of the illustrative embodiments may be implemented. It should be appreciated that FIGS. 1-2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. The distributed data processing system may include a network of computers in which aspects of the illustrative embodiments may be implemented. The distributed data processing system contains at least one network 102, which is the medium used to provide communication links between various devices and computers connected together within the distributed data processing system. The network 102 may include connections, such as wire, wireless communication links, or fiber optic cables.

In the depicted example, servers 104 and server 105 are connected to network 102 along with storage unit 106. In addition, clients 110 and 112 are also connected to network 102. These clients 110 and 112 may be, for example, personal computers, network computers, or the like. In the depicted example, servers 104 and 105 may provide data, such as boot files, operating system images, and applications, to the clients 110 and 114. Clients 110 and 112 are clients to servers 104 and 105 in the depicted example. The distributed data processing system may include additional servers, clients, and other devices not shown.

In the depicted example, the distributed data processing system is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system may also be implemented to include a number of different types of networks, such as an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., server 105, may be specifically configured to implement an analytics system 100 having, as one component, a dashboard usage tracking and recommendation system 130 that operates as described hereafter in conjunction with other elements of the analytics system 100 to track and analyze dashboard usage and provide recommendations as to other dashboards a user may access to obtain the information the user seeks as well as provide recommendations as to improvements that may be made to the set of dashboard offerings provided. The configuring of the computing device, e.g., server 105, may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 105, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described hereafter, the implementation of the mechanisms of the illustrative embodiments improves the functionality of the computing device and provides a useful and concrete result that facilitates providing guidance to users as to dashboards where predictive analytics determine that the information sought by the user may be obtained as well as providing recommendations, such as to system administrators or other providers of dashboards, as to dashboard modifications or new dashboards that could be generated to provide information that the user and/or other users of the same or different organizations, tend to seek when accessing pre-defined existing dashboards.

As shown in FIG. 1, the server 105, which may represent a single or multiple server computing devices (e.g. a server farm or other collection of computing resources), is configured to provide an analytics system 100 that operates to receive data from data sources, such as servers 104 associated with one or more organizations, via network 102 and process the data to generate analytics and statistical data about a subject of interest which may then be output via one or more dashboards to users, such as via client computing devices 110 and 112. For example, healthcare related data may be obtained from servers 104 which may be associated with different healthcare provider organizations, e.g., a first server 104 may be associated with a hospital, a second server 104 may be associated with a pharmacy, a third server 104 may be associated with a doctor office, a fourth server 104 may be associated with a health insurance provider, etc. The healthcare data may include various types of data including, but not limited to, patient electronic medical records (EMR) data, health insurance claims data, pharmacy prescription fulfillment data, and the like. Any type of healthcare related data from any type of healthcare data source may be utilized with the mechanisms of the illustrative embodiments.

The data obtained from the various source systems 104, and even network attached storage 106, may be provided to the server 105 for processing by the analytics system 100. In some cases, pre-processing of the raw data obtained from these source systems 104 may be performed by the server 105 so as to place the data in a proper format for use by the analytics system 100, as well as standardize the data because of the differences in different systems 104, e.g., map medical codes to a common set of medical codes, etc. The pre-processed data may then be stored in backend data stores 150 for access by the analytics system 100 which performs analytics on the data with the results data also being able to be stored in the backend data stores 150 for use.

It should be appreciated that the term "analytics" as used herein refers to the use of mathematics, statistics, predictive modeling, and machine learning techniques to find meaningful patterns and knowledge in stored data. The "analytics" may be implemented through one or more analytics systems 110 which provide algorithms to process data stored in the backend data stores and generate analytics results data which represent the meaningful patterns and knowledge obtained from the pre-processed data obtained from the various source systems 104. The analytics may be applied within a single organization or across multiple organizations, and may combine analysis of data from one or a plurality of source systems 104.

The analytics systems 110 generate analytics results data which again, may be stored in the backend data stores 150, or in other storage (not shown) for utilization in providing output representations of the results data, e.g., graphical, textual, or audible outputs presenting the analytics results data for use by a user. The user experience systems 120 provide the logic for generating these output representations which, in accordance with the illustrative embodiments described herein, include one or more dashboards. A "dashboard" as the term is used herein refers to a graphical and/or textual user interface that provides a plurality of different representations of the same or different analytics results data in a single output, as previously discussed above. The particular dashboards that the user experience systems 120 may generate are pre-defined by dashboard creators and stored in a dashboard repository (not shown) associated with the user experience systems 120. The pre-defined dashboards are populated with specific data obtained from the analytics results data generated by the analytics systems 110 and stored in the backend data stores 150 or other storage, which is accessible via the backend data store interface system 140, and which may also provide the pre-processors and other logic for maintaining data in the backend data stores 150 and providing access to such stored data.

The dashboard usage tracking and recommendation system 130 provides the logic for tracking user interactions with the various dashboards that are provided by the user experience systems 120 as well as interactions the users make both before and after interacting with the dashboards so as to generate a usage pattern for the user. The usage pattern is a representation of the types of actions performed by the user with the dashboard, lengths of time interacting with elements of the dashboard, and/or actions taken prior to or subsequent to interacting with the dashboard such as with other user experience systems 120 including, but not limited to, search engines, instant messaging systems, and the like. The usage patterns are associated with dashboards provided by the user experience systems 120 and indicate the way that the user is using the dashboard and/or indications of other information that the user was not able to obtain from the dashboard.

For example, a user may wish to obtain average cancer treatment claims information for a particular geographical region. The user may request a "Cancer Claims" dashboard, but finds that the dashboard does not provide the particular cancer treatment claims information broken down by geographical region. The user may then access a different dashboard, entitled the "Claims by Geographical Region" dashboard, but which may not present claims information broken down into specific disease types. Thereafter, the user may perform a search through a search engine for "Cancer Claims by Region" and may instant message a colleague asking "Do you know where I can get information on cancer claims per region?" All of these actions may be recorded by the mechanisms of the illustrative embodiments for the user session such that these actions are tracked and may then be analyzed to identify a usage pattern for the user session that indicates that the user used the particular dashboards, appears to be looking for cancer claims information for geographical regions, and was not able to find that information in the specific dashboards accessed. Moreover, the mechanisms of the illustrative embodiments may record timestamp information for the actions to show how long the user viewed the various dashboards which may indicate the relative usefulness of the dashboards with regard to providing information similar to what the user was looking for, i.e., a user may view a dashboard for a longer period of time if the information is of use for the user's purposes compared to a dashboard that is clearly not useful.

Based on the usage patterns identified in the user session, the dashboard usage tracking and recommendation system 130, using predictive analytics based on the recorded action information, keywords in searches, keywords in instant messages, and any other indicators specific to the implementation, determines the information that the system 130 predicts the user is attempting to obtain. The indicator of the information determined from the predictive analytics, e.g., "Cancer Claims for a Geographical Region," is compared to dashboard characteristics for the pre-defined dashboards to determine whether any pre-defined dashboard provides the information that the predictive analytics predict the user is attempting to access. The dashboard characteristics may be defined when the dashboard is created and may specify the types of information presented in the dashboard as well as the manner by which the information is presented, e.g., bar graph, pie chart, numerical representation, etc., and other dashboard characteristics that are pertinent to defining the type of dashboard and its content. If one or more dashboards exist that have dashboard characteristics that match the identifier of the information predicted to be sought by the user, then those dashboard(s) are selected as potential recommendations to be presented to the user.

The dashboard usage tracking and recommendation system 130 may then generate a recommendation output that is output to the user and includes an indication of the information that the system 130 predicts the user is looking for as well as the recommended dashboard(s) for providing the information. Moreover, the output may include hyperlinks, graphical user interface elements, or the like, for allowing the user to select or otherwise specify a desire to go to a recommended dashboard and have it provided to the user.

In addition to recommendations provided for individual users during user sessions with the analytics system 100, the dashboard usage tracking and recommendation system 130 may further provide usage tracking and analysis across multiple users in the same and/or different organizations and provide recommendations to system administrators and/or other dashboard creators as to the usage patterns observed across multiple users with regard to the pre-defined dashboards. For example, analytics may be executed on user interaction data tracked for each of the pre-defined dashboards to extract information about the way in which the users utilized the dashboards and the actions that they take both before and after interacting with the dashboards indicating the usefulness of the dashboard to the users' needs. For example, an analytic may indicate that users of dashboard A tend to go to dashboard B after viewing dashboard A, indicating that dashboard B may provide information that users were hoping to find in dashboard A. Moreover, user interactions with dashboard B may be recorded to see what portions of dashboard B the users interacted with after having gone to dashboard B from dashboard A, e.g., the user drills down into the underlying analytics data used to generate a particular portion of dashboard B.

As a result, differences between the information presented in dashboard B and dashboard A may be identified and a recommendation to modify dashboard A to include a link to dashboard B or to include portions of dashboard B in dashboard A may be generated. For example, the highest frequency of occurrences of interactions between a user and other dashboards, e.g., dashboard B, or other user experience systems 120, e.g., instant messaging system(s), search engine(s), etc., and/or portions thereof, that are associated with the dashboard being analyzed, e.g., dashboard A, may be utilized to generate recommendations as to additions or modifications to be made to the dashboard being analyzed. For example, based on the portions of another dashboard manipulated by user input subsequent to the dashboard being analyzed, e.g., dashboard A, and correlating information about those portions that indicates the type of analytics data represented in those portions as well as the way in which the analytics data may be represented in the dashboard, a recommendation that similar types of analytics data should be included in the dashboard being analyzed and a recommendation as to the way in which the analytics data may be represented in the dashboard may be provided. In some cases, the actual portion of code used to represent the portion of the other dashboard may be provided as an example portion of code to include in the dashboard code for the dashboard being analyzed, e.g., dashboard A.

Similarly, analyzing the frequency of occurrence of search terms searched by users prior to or following the user's interactions with the dashboard being analyzed may identify terms representing analytics data that the users are attempting to gain access to and may be a basis for correlating with the metadata indicating the types of analytics data represented in other dashboards. A similar approach may be performed using natural language processing of instant messages and other types of communications conducted by users via the user experience systems 120 to thereby identify terms and/or phrases that users use most frequently in combination with their interactions with a particular dashboard being analyzed. These terms/phrases may be used to correlate with metadata or other information describing the types of analytics data represented in the various dashboards. From this correlation, recommendations as to links to other dashboards and/or portions of other dashboards that may be included in the dashboard being analyzed may be generated and output to a dashboard creator and/or provider of dashboards as part of the analytics system 100.

It should be appreciated that these are only examples of recommendations that may be generated using the mechanisms of the illustrative embodiments. The actual coding and/or inclusion of recommendations into the dashboards may be performed using known or later developed dashboard authoring tools. Other types of recommendations may be generated using the mechanisms of the illustrative embodiments without departing from the spirit and scope of the present invention.

As noted above, the mechanisms of the illustrative embodiments utilize specifically configured computing devices, or data processing systems, to perform the operations for tracking dashboard usage patterns and providing various levels of dashboard recommendations to the user and/or system administrator or other dashboard provider. These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external affects of the illustrative embodiments as described herein.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System P® computer system, Power™ processor based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as main memory 208, ROM 224, or in one or more peripheral devices 226 and 230, for example.

A bus system, such as bus 238 or bus 240 as shown in FIG. 2, may include one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for execution by one or more hardware processors, such as processing unit 206, or the like. As such, the computing device shown in FIG. 2 becomes specifically configured to implement the mechanisms of the illustrative embodiments and specifically configured to perform the operations and generate the outputs described herein with regard to one or more illustrative embodiments directed to the tracking of dashboard usage data for users and providing dashboard recommendations based on analysis of the tracked dashboard usage data and actions of users surrounding their interactions with the dashboards.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3A is an example block diagram of the primary operational elements of a dashboard usage tracking and recommendation system in accordance with one illustrative embodiment. The example shown in FIG. 3 is an example of an implementation of one illustrative embodiment that operates on healthcare data obtained from a plurality of healthcare data systems 310, e.g., doctor office computer systems, hospital computer systems, pharmacy computer systems, health insurance computer systems, government healthcare agency computer systems, or the like. It should be appreciated that this is only one illustrative embodiment and one example of a domain in which the mechanisms of the illustrative embodiments may be implemented. Any domain in which dashboards are utilized to represent analytics data generated from the application of analytics to raw data obtained from one or more source systems may be used with the mechanisms of the illustrative embodiments without departing from the spirit and scope of the present invention.

As shown in FIG. 3A, raw healthcare data from systems 310 may be received by the analytics system 300 and optionally subjected to data pre-processing system(s) 312 to pre-process the raw data and generate pre-processed data that may be stored in the backend data stores 320. It should be appreciated that in some implementations pre-processing may not be necessary and instead the raw data may in fact be stored in the backend data stores 320. The raw data may be received from the healthcare data systems 310 via one or more data networks, for example, with the pre-processing systems 312 performing operations to standardize or otherwise re-format the data for use by the analytics system 300 since the various healthcare data system(s) 310 may each utilize their own desired formats, references (e.g., medical codes, etc.), and other types of data that may need to be mapped to a common or standardized format that correlates information from the various healthcare data system(s) 310. The raw data may represent any type of healthcare related data that is pertinent to the particular implementation, such as electronic medical records (EMRs) of patients, admissions information from hospitals, insurance claims information, prescription information from pharmacy systems, instance information for particular disease reports from a governmental agency, or the like.

Figure 4:
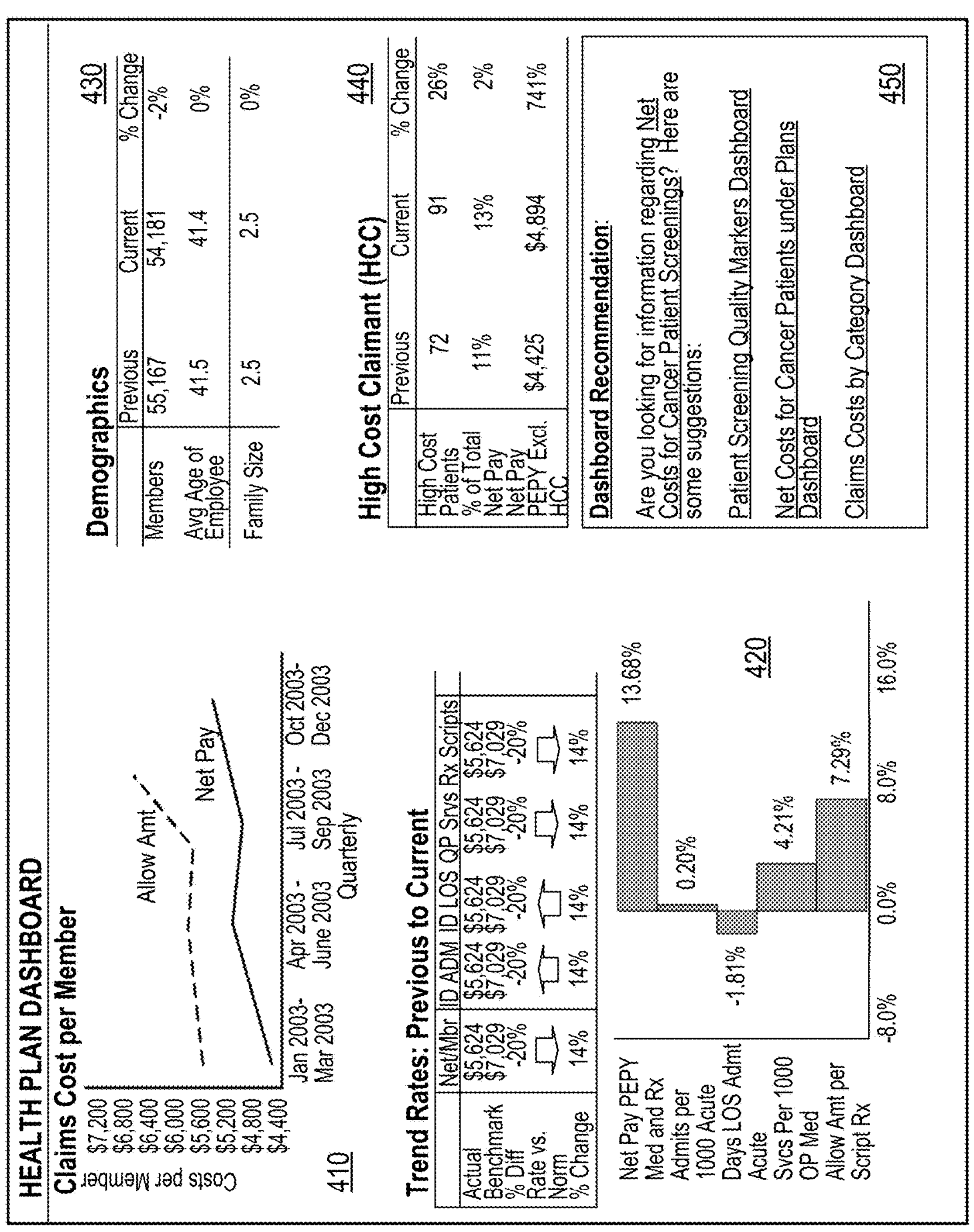
FIG. 4 is an example diagram of a dashboard output with a dashboard recommendation portion in accordance with one illustrative embodiment.

The pre-processed data stored in the backend data stores 320, and/or raw data depending on the particular implementation, may be provided to analytics engines 330 for the performance of analytics operations to generate analytics results data that may be stored in the backend data stores 320 and/or provided to the user experience system 340. The analytics engines 330 may perform various analytical analyses on the pre-processed and/or raw data to generate meaningful patterns and knowledge. For example, the raw or pre-processed healthcare data may be analyzed by analytics engines 330 to generate such values as claims costs per member per time period, trend rate information, various types of demographics information analytics, high cost claimant information, or the like, examples of which are shown in FIG. 4 discussed hereafter.

The analytics data generated by the analytics engine(s) 330 may be provided, either from the backend data stores 320 or directly from the analytics engines 330, to the user experience system 340 which comprises logic for generating one or more dashboards 360 based on predefined dashboard data structures in predefined dashboards storage 345. The predefined dashboard data structures may specify templates, code, or utilized other mechanisms for defining the dashboards including the portions of the dashboards, the analytics data used to generate the portions of the dashboards, and the like. The user experience system 340 may, based on a request from a user via a client system 370 or administrator console 380, generate a corresponding dashboard that matches the request by retrieving the appropriate predefined dashboard data structure from the storage 345 and populating the portions of the dashboard 360 with analytics data generated by the analytics engines 330. The request may specify criteria for the analytics data to use when generating the dashboard 360, e.g., a time frame, patient characteristics data, geographic region, etc. which may thereby be used to filter the analytics data represented in the dashboard 360.

The generated dashboards 360 are provided to the client systems 370 and user interactions with the dashboards 360 may be monitored by the dashboard usage tracking and recommendation (DUTAR) system 350. While the DUTAR system 350 is shown as being part of the user experience system 340, the DUTAR system 350 may also be separate from the user experience system 340 yet part of the analytics system 300.

The DUTAR system 350 provides logic for listening to the user inputs to dashboards and/or other user experience systems 365, such as search engines, instant messaging systems, and the like, to log and/or record user inputs both before, during, and after interacting with a dashboard of interest. The DUTAR system 350 may utilize agents 375, i.e. portions of code designed to log and transmit information about user interactions with user experience systems, deployed on client systems to obtain the user input information tracking the user's input patterns. In this way, the user's input patterns may be identified before, during, and after a dashboard is provided to the user which may then be indicative of the type of data the user is attempting to access. This information may be utilized by predictive analytics logic 357 of the DUTAR system 350 to predict what type of data or information the user is attempting to access and generate a recommendation for the user. Moreover, the input patterns of the user may be accumulated with other input pattern data for the particular dashboard and stored in the dashboard usage data storage 355 for presentation of dashboard usage metrics information and/or recommendations as to how to improve dashboard offerings via administrator consoles 380.

The recommendations for the user during a user session with a dashboard 360 may be generated based on the predictive analytics of predictive analytics logic 357 in the DUTAR system 350 and may be presented to the user via client system 370 either as a separate recommendation or as a recommendation integrated with a presented dashboard 360. The recommendation, as noted above, may be generated by comparing the identifier of the predicted data or information that the predictive analytics logic 357 of the DUTAR system 350 determines the user is looking for, to identifiers of data or information presented in various ones of the predefined dashboards 345 based on the metadata associated with the various predefined dashboard data structures in the storage 345. Those dashboards data structures having metadata that have identifiers matching that of the predicted data or information may be returned, as part of search results generated from searching the predefined dashboards 345 based on the predicted data or information identifier(s), to the DUTAR system 350 and a corresponding recommendation recommending those returned dashboards is generated and sent to the client system 370. As noted above, this recommendation may be in the form of a suggestion with corresponding links or other mechanisms for allowing a user to access the recommended dashboards from the recommendation output.

The dashboard usage data 355 stores cumulative usage metric information for each predefined dashboard in the storage 345 indicating various characteristics of user inputs associated with the predefined dashboard which may also be correlated with particular user characteristics information stored in the user registry 356, such as may be part of a user profile data structure or the like. For example, the metrics information may indicate the number of users that have input certain search terms into search engines before or after using the dashboard, metrics of how many times users accessed portions of the particular dashboard, metrics of how many times users accessed each of one or more other pre-defined dashboards either before or after accessing the dashboard of interest, metrics of the number of times users used certain terms or phrases during instant messaging within a predefined time period before or after accessing the dashboard of interest, or the like. These metrics may be presented to an administrator via one or more administrator consoles 380.

Moreover, the DUTAR system 350 may also analyze these metrics and present recommendations to the administrator as to modifications to the dashboard of interest. For example, as noted above, highest occurrences of particular terms or phrases may be matched to terms/phrases in metadata descriptions of pre-defined dashboards in the storage 345 to determine which pre-defined dashboard data structures present information related to those terms/phrases. Similarly, based on the determination of portions of other dashboards, or dashboards themselves, accessed by users more often than other dashboards or portions thereof, recommendations as to modifications to the dashboard of interest to include a link to or portions of the other dashboard may be generated. All of this information may be presented to an administrator so that the administrator can determine what modifications, if any, to perform to a dashboard so as to improve the dashboard offerings provided in the predefined dashboards storage 345.

In some illustrative embodiments the DUTAR system 350, e.g., the predictive analytics logic 357 of the DUTAR system 350, may predict dashboards that may be of interest to a particular user based on clustering of similar users based on the user registry 356 as well as information in the dashboard usage data 355 indicating which users access the same dashboard. For example, for a user that has accessed dashboard A, other users that have accessed dashboard A may be retrieved from the dashboard usage data 355 which may log identifiers of users that have accessed each of the dashboards over a predetermined period of time. Based on the identification of other users that have accessed the same dashboard as the present user, i.e. dashboard A, corresponding user characteristic information from user registry 356 may be obtained. Users with similar characteristics may be clustered together and the dashboard usage data 355 for the other users in the same cluster as the present user may be accessed to determine what other dashboards the other users accessed which the present user has not accessed yet. These other dashboards may be identified as dashboards that may be recommended to the present user for potentially providing the information or data sought by the present user.

Figure 3B:
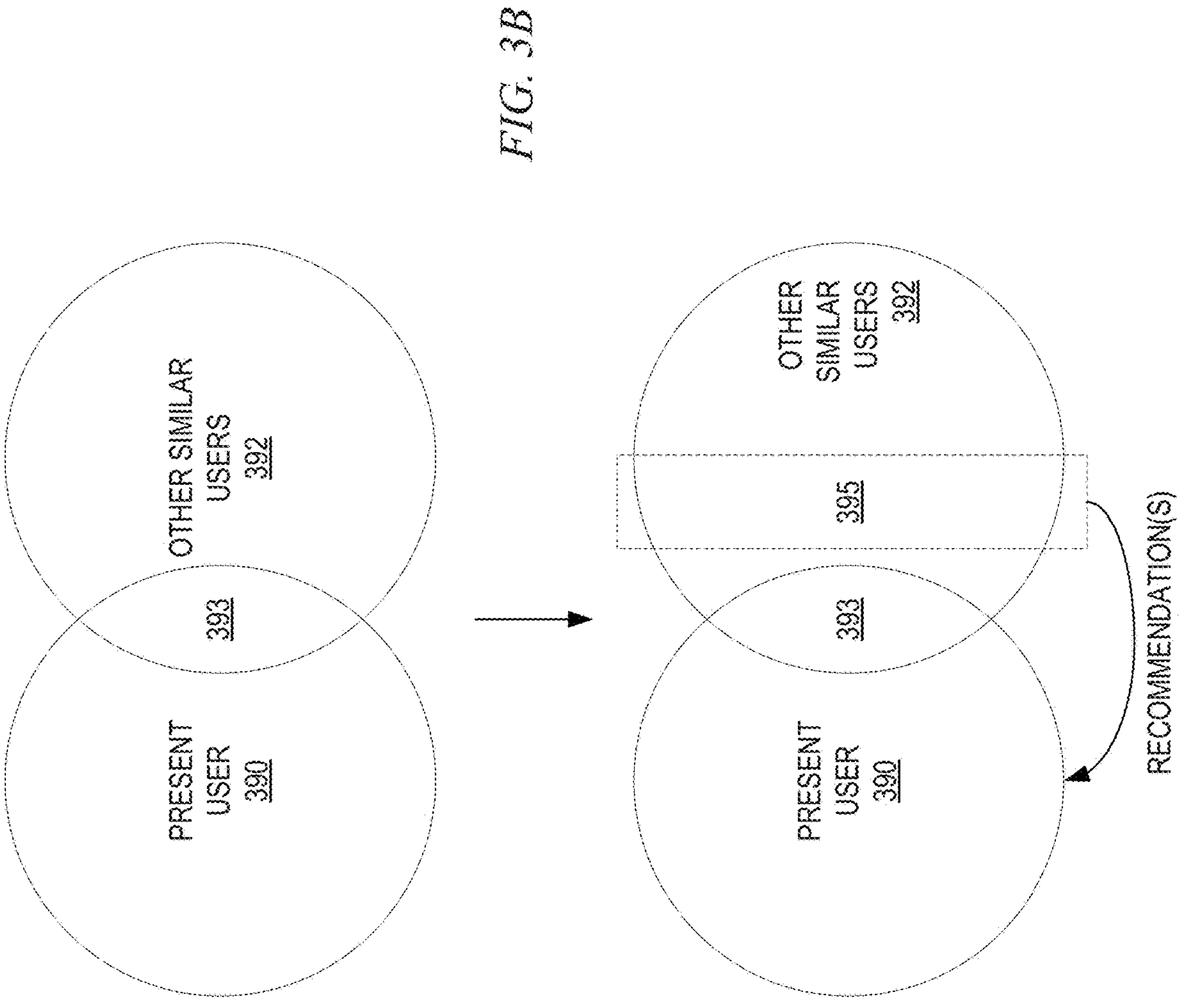
FIG. 3B is an example diagram illustrating one example operation for identifying dashboards accessed by similar users for purposes of generating recommendations for a user in accordance with one illustrative embodiment.

An example of this operation is represented in FIG. 3B. As shown in FIG. 3B, the example operation for identifying dashboards accessed by similar users for purposes of generating recommendations depicted models a single user's behavior and compares this behavior to other users with similar characteristics to form a recommendation based on like users. For example, as shown in FIG. 3B, two sets of dashboards accessed by the present user 390 and other users 392 are conceptually represented with an overlap region 393 representing dashboards that both the present user 390 and the other users 392 have accessed while the other non-overlap regions represent dashboards not accessed by both the present user 390 and the other users 392.

A portion 395 of the dashboards accessed by the other users 392 may be selected for use in generating recommendations to the present user. This portion 395 may be selected in a variety of different ways based on the dashboard usage data 355. For example, the portion 395 may be selected based on the set of dashboards in the other users 392 set that a predetermined number of the other users have accessed, e.g., if dashboard B is accessed by 30% or more of the other users 392, then dashboard B may be selected as a recommendation. In other illustrative embodiments, those dashboards that were accessed within the same session as dashboard A may be selected as recommendations. Any suitable criteria for selecting dashboards accessed by other similar users to the present user, which have not been accessed by the present user yet during the present session, may be used without departing from the spirit and scope of the present invention. Of course other methodologies and algorithms for selecting a sub-set of the dashboards in the similar users 392 set may be used without departing from the spirit and scope of the present invention.

As touched upon above, in some illustrative embodiments, recommendations may be constructed based on the user's behavior as it relates to their interactions with other user experience systems and, in some cases, the subject matter of the content that the user accessed via these other user experience systems. For example, a recommendation may be constructed based on a user's behavior as it relates to their consumption of whitepapers versus time spent on specific dashboards. If a user has read multiple whitepapers related to prescription medication cost drivers, for example, and has spent a significant amount of time interacting with a prescription medication cost dashboard, as may be indicated by the dashboard usage data 355 in comparison to one or more threshold values defining a "significant" amount of time, the DUTAR system 350 may recommend other dashboards tied to the cost of prescription medications.

For example, assume that a user spends time reading whitepapers, via another user experience system 365, related to prescription drug costs for the drug Enbrel and interacting with a dashboard designed to show how much the user's organization is currently spending on prescription medication. A recommendation would then occur for dashboards tied to the drug Enbrel and/or dashboards tied to the cost effective treatment of rheumatoid arthritis, i.e. a medical condition that is treated with the drug Enbrel.

Of course, combination approaches may also be applied when generating recommendations, where these combination approaches combine similar user dashboard usage information with user behavior information to generate recommendations for a user. Moreover, recommendations made for one user may also be logged in the dashboard usage data 355 and/or as part of a user's profile in the user registry 365, and used as a basis for generating recommendations for other users having similar characteristics or similar dashboard usage behavior patterns. For example, a rheumatoid arthritis dashboard may be recommended to the present user even though the user has not exhibited the above behavior of reading white papers focused on Enbrel, but who does instead have enough similarities with other users for which a rheumatoid arthritis dashboard was recommended, such as by using one of the implementations above.

These are but examples of ways in which the logic of the DUTAR system 350 may generate recommendations for users based on the tracked information in the dashboard usage data 355 and/or the user profile information in the use registry 356. Other ways of implementing logic for generating recommendations based on analysis of the tracked information may occur to those of ordinary skill in the art in view of the present description. These other ways of implementing such logic are intended to be within the spirit and scope of the present invention and the present description.

Thus, the illustrative embodiments provide mechanisms for tracking user usage of dashboards and providing recommendations as to where the users can obtain information that the users appear to be attempting to access. These mechanisms utilized predictive analytics to determine what information or data the user is attempting to access based on the pattern of inputs the user provides before, during, and/or after the presentation of a dashboard. Based on the prediction, metadata associated with pre-defined dashboards may be searched to identify other dashboards that provide the predicted data or information being sought by the user. In addition, dashboard usage metrics may be accumulated across multiple users for each dashboard and used to present information to an administrator as well as may be used as a basis for generating recommendations to an administrator as to ways to improve the dashboard offerings in the predefined dashboards storage 345.

FIG. 4 is an example diagram of a dashboard output with a dashboard recommendation portion in accordance with one illustrative embodiment. As shown in FIG. 4, the dashboard 400 includes a plurality of portions 410-440 for presenting different types of analytics results data or presenting the analytics results data in different ways. The presentation of the analytics results data may take many different forms, including graphs, charts, numerical values, text, and the like, with each individual portion 410-440 of the dashboard potentially presenting corresponding analytics results data in different ways or in different formats. For example, portion 410 in FIG. 4 presents a line graph to represent claims costs per member. Portion 420 presents a bar graph of trend rates. Portion 430 provides a chart with demographics information and portion 440 presents a chart with high cost claimant information.

In accordance with the mechanisms of the illustrative embodiments, based on the operation of the dashboard usage tracking and recommendation system 130, 350 of the analytics system 100, 300 described above, the dashboard 400 includes a portion 450 for outputting dashboard recommendations for the user. While this portion 450 is shown as part of a dashboard 400, it should be appreciated that the portion 450 may in fact be separate from any dashboard, such as in the case of a pop-up window, instant message, or any other mechanism by which to present an output of a dashboard recommendation to a user.

As shown in FIG. 4, the portion 450 includes an identifier of the information that the dashboard usage tracking and recommendation system 130, 350 predicts, via its predictive analytics on the dashboard tracking data, the user is attempting to access, e.g., in the depicted example, the system 130, 350 predicts that the user is attempting to access information regarding "Net Costs for Cancer Patient Screenings" and outputs a message asking the user if the user is looking for this information. The portion 450 further includes a listing of recommended dashboards that provide the information that the system 130, 350 predicts the user is attempting to access. This listing may include hyperlinks to the dashboards or other user interface elements for allowing the user to select a corresponding entry in the listing so as to immediately access the recommended dashboard.

It should be appreciated that the depiction in FIG. 4 is only an example. Many modifications may be made to the depiction in FIG. 4 without departing from the spirit and scope of the present invention.

FIG. 5 is a flowchart outlining an example operation for providing a dashboard recommendation to a user based on dashboard tracking and analysis in accordance with one illustrative embodiment. The operation outlined in FIG. 5 may be implemented, for example, by a dashboard usage tracking and recommendation system 130, 350 described above with regard to FIGS. 1 and 3. As such, the system 130, 350 may operate in conjunction with other logic and systems to provide input data upon which the system 130, 350 operates and with which the system 130, 350 communicates to provide outputs and receive inputs.

As shown in FIG. 5, the operation starts with the receipt of a consumer (or user) request for dashboard(s) during a current session (step 510). Instance(s) of the dashboard(s) are generated using the particular consumer's data (step 520) and the user interactions with the dashboard(s) as well as actions taken before and after interacting with the dashboard(s) are tracked for the session, which are collectively referred to as tracked user interactions (step 530). Analytics are applied to the tracked interaction data to identify one or more usage patterns (step 540). Based on the usage patterns, a prediction of the types of data the user is attempting to access is generated (step 550).

Based on the predicted types of data the user is attempting to access, pre-defined dashboards that provide the predicted types of data, or portions of pre-defined dashboards that provide the predicted types of data, are identified, such as via matching with dashboard characteristics information associated with the pre-defined dashboards (step 560). Dashboard recommendations are then generated based on the correlation of the predicted types of data being sought by the user with the dashboard characteristics of the various dashboards or portions thereof (step 570). The recommendations are then output to the user via a user interface, which in one implementation may be a currently viewed dashboard, or a pop-up window, or other output message mechanism (step 580). The operation may then receive user input to the recommendation output and provide a user selected recommended dashboard in response to the user selection to go to the recommended dashboard (step 590). The operation may then terminate.

FIG. 6 is a flowchart outlining an example operation for generating administrative consoles for providing dashboard recommendations across multiple users and/or organizations in accordance with one illustrative embodiment. Again, the operation outlined in FIG. 6 may be implemented, for example, by a dashboard usage tracking and recommendation system 130, 350 described above with regard to FIGS. 1 and 3. As such, the system 130, 350 may operate in conjunction with other logic and systems to provide input data upon which the system 130, 350 operates and with which the system 130, 350 communicates to provide outputs and receive inputs.

As shown in FIG. 6, the operation starts by retrieving dashboard usage tracking and/or recommendation information across a plurality of consumers (or users) associated with the same or different organizations (step 610). The usage tracking and/or recommendation information is analyzed to identify usage patterns across consumers (step 620).

The usage patterns identified are correlated with dashboards or portions of dashboards (step 630) and recommendations are generated for modifying dashboards or generating new dashboards to address the usage patterns (step 640). The recommendations are then used as a basis for generating and outputting administrative consoles with the dashboard recommendations, usage pattern data, and results of the analysis/correlation of the usage pattern data with dashboards or portions thereof (step 650). The operation then terminates.

Thus, the illustrative embodiments provide mechanisms for tracking usage of dashboards and, via predictive analytics, identify types of information that users are attempting to access via the dashboards and providing them with recommendations as to other dashboards that may provide the information that they seek. The illustrative embodiments further provide mechanisms for analyzing usage patterns of users across one or more organizations to identify improvements that may be made in the dashboard offerings of these organizations. In this way, users are provided with recommendations as to where they may find the information that they appear to be looking for and thereby reduce frustration due to an inability to find the information they seek. Moreover, organizations are presented with recommendations as to how to improve upon the representations of analytics data via dashboards so as to reduce frustration and improve productivity of the users in their organizations at a larger scale.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth® wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method, in a data processing system including at least one memory and at least one processor, wherein the at least one memory includes instructions that are executed by the at least one processor to configure the at least one processor to implement the method, the method comprising:

presenting, on a client computing device, a first dashboard providing a graphical user interface to a first user;

tracking user inputs to the client computing device, at least during and after presentation of the first dashboard to the first user, to identify at least one characteristic of the user inputs;

generating predictive analytics by applying logic to: identify and analyze dashboard usage patterns associated with one or more other users that accessed the first dashboard and transitioned from the first dashboard to one or more other dashboards, and interactions of the one or more other users with portions of the one or more other dashboards, and to identify and analyze user characteristics associated with the one or more other users;

applying the predictive analytics to the tracked user inputs to predict a type of data the first user is attempting to access and that is not provided by the first dashboard;

correlating the predicted type of data with the one or more portions of the one or more other dashboards, wherein the one or more portions of the one or more other dashboards provide a representation of data having a type matching the predicted type of data that is not provided by the first dashboard;

outputting a recommendation to the first user via an interactive graphical user interface element indicating the one or more correlated portions of the one or more other dashboards providing the representation of data matching the predicted type of data that is not provided by the first dashboard;

receiving a user selection of the recommendation via the interactive graphical user interface element; and in response to the user selection, modifying the first dashboard to display the predicted type of data by incorporating into the first dashboard the one or more correlated portions of the one or more other dashboards.

2. The method of claim 1, wherein presenting the first dashboard comprises:

Receiving input data from one or more source computing systems via one or more data networks;

analyzing the input data to generate analytics results data; and generating-the first dashboard by populating portions of a dashboard data structure with corresponding portions of the analytics results data to generate a plurality of data representations within the first dashboard.

3. The method of claim 1, wherein tracking user inputs to the client computing device comprises tracking user inputs to user interface elements of the first dashboard and tracking user inputs to at least one other user experience system providing another user interface for accessing content or exchanging information with another user.

4. The method of claim 3, wherein the at least one other user experience system comprises at least one of a search engine user interface or an electronic messaging user interface.

5. The method of claim 4, wherein tracking user inputs to the at least one other user experience system comprises extracting key terms or key phrases entered by the first user into the search engine user interface or electronic messaging user interface, and wherein correlating the predicted type of data with the one or more portions of the one or more other dashboards comprises searching metadata associated with the one or more other dashboards based on the extracted identified key terms or key phrases to identify the one or more other dashboards as having at least one matching key term or key phrase in the metadata as the extracted key terms or key phrases.

6. The method of claim 1, wherein the outputting the recommendation to the first user comprises outputting a portion of the first dashboard or another user interface having user selectable links that, when selected by the first user, access a corresponding one of the one or more other dashboards.

7. The method of claim 1, further comprising:

storing, for the first dashboard, tracked usage metrics based on tracking the user inputs to the client computing device cumulatively with other user inputs to the first dashboard;

generating a dashboard recommendation based on the cumulatively stored tracked usage metrics; and outputting the dashboard recommendation to a system administrator.

8. The method of claim 1, wherein correlating the predicted type of data with one or more portions of one or more other dashboards comprises:

creating a cluster of the one or more other users having at least one matching characteristic to the first user based on the analyzed user characteristics associated with the one or more other users; and generating the recommendation based on the one or more other dashboards accessed by at least some of the users in the cluster.

9. The method of claim 8, wherein generating the recommendation based on the one or more other dashboards accessed by at least some of the users in the cluster comprises:

identifying at least one of the one or more other dashboards accessed by the at least some of the users in the cluster which provides a representation of data having a type matching the predicted type of data, and which has not been previously accessed by the first user during a current user session.

10. The method of claim 1, wherein the identified at least one characteristic includes at least one key text portion extracted from a text input of the user inputs, and wherein the correlating the predicted type of data with one or more portions of one or more other dashboards further comprises performing a search of metadata of a plurality of dashboards based on the extracted key text portion and selecting the one or more other dashboards based on a matching of the key text portion with content in metadata associated with the one or more other dashboards.

11. The method of claim 1, wherein one or more of: the first dashboard; or the one or more other dashboards, are predefined.

12. The method of claim 1, wherein the recommendation is displayed in the first dashboard or as a pop-up window.

13. The method of claim 1, wherein the recommendation is stored in the at least one memory as user characteristic information associated with the first user.

14. The method of claim 1, wherein the dashboard usage patterns are identified based on at least a threshold number of the one or more other users that accessed the first dashboard and transitioned from the first dashboard to the one or more other dashboards.

15. A computer program product including a computer readable storage medium having a computer readable program stored therein, wherein the computer readable program, when executed on a computing device, causes the computing device to:

present, on a client computing device, a first dashboard providing a graphical user interface to a first user;

track user inputs to the client computing device, at least during and after presentation of the first dashboard to the first user, to identify at least one characteristic of the user inputs;

generate predictive analytics by applying logic to: identify and analyze dashboard usage patterns associated with one or more other users that accessed the first dashboard and transitioned from the first dashboard to one or more other dashboards, and interactions of the one or more other users with portions of the one or more other dashboards, and to identify and analyze user characteristics associated with the one or more other users;

apply the predictive analytics to the tracked user inputs to predict a type of data the first user is attempting to access and that is not provided by the first dashboard;

correlate the predicted type of data with the one or more portions of the one or more other dashboards, wherein the one or more portions of the one or more other dashboards provide a representation of data having a type matching the predicted type of data that is not provided by the first dashboard;

output a recommendation to the first user via an interactive graphical user interface element indicating the one or more correlated portions of the one or more other dashboards providing the representation of data matching the predicted type of data that is not provided by the first dashboard;

receive a user selection of the recommendation via the interactive graphical user interface element; and in response to the user selection, modify the first dashboard to display the predicted type of data by incorporating into the first dashboard the one or more correlated portions of the one or more other dashboards.

16. The computer program product of claim 15, wherein the computer readable program causes the computing device to present the first dashboard at least by:

receiving input data from one or more source computing systems via one or more data networks;

analyzing the input data to generate analytics results data; and generating the first dashboard by populating portions of a dashboard data structure with corresponding portions of the analytics results data to generate a plurality of data representations within the first dashboard.

17. The computer program product of claim 15, wherein the computer readable program causes the computing device to track user inputs to the client computing device at least by tracking user inputs to user interface elements of the first dashboard and tracking user inputs to at least one other user experience system providing another user interface for accessing content or exchanging information with another user.

18. The computer program product of claim 17, wherein the at least one other user experience system comprises at least one of a search engine user interface or an electronic messaging user interface.

19. The computer program product of claim 18, wherein the computer readable program causes the computing device to track user inputs to the at least one other user experience system at least by extracting key terms or key phrases entered by the first user into the search engine user interface or electronic messaging user interface, and wherein the computer readable program causes the computing device to correlate the predicted type of data with the one or more portions of the one or more other dashboards at least by searching metadata associated with the one or more other dashboards based on the extracted key terms or key phrases to identify the one or more other dashboards as having at least one matching key term or key phrase in the metadata as the extracted key terms or key phrases.

20. The computer program product of claim 15, wherein the computer readable program further causes the computing device to:

store, for the first dashboard, tracked usage metrics based on tracking the user inputs to the client computing device cumulatively with other user inputs to the first dashboard;

generate a dashboard recommendation based on the cumulatively stored tracked usage metrics; and output the dashboard recommendation to a system administrator.

21. The computer program product of claim 15, wherein the computer readable program causes the computing device to correlate the predicted type of data with one or more portions of one or more other second dashboards at least by:

creating a cluster of the one or more other users having at least one matching characteristic to the first user based on the analyzed user characteristics associated with the one or more other users; and generating the recommendation based on the one or more other dashboards accessed by at least some of the users in the cluster.

22. The computer program product of claim 21, wherein the computer readable program causes the computing device to generate the recommendation based on the one or more other dashboards accessed by the at least some of the users in the cluster at least by:

identifying at least one of the one or more other dashboards accessed by the at least some of the users in the cluster which provides a representation of data having a type matching the predicted type of data, and which has not been previously accessed by the first user during a current user session.

23. The computer program product of claim 15, wherein the identified at least one characteristic includes at least one key text portion extracted from a text input of the user inputs, and wherein the correlating the predicted type of data with one or more portions of one or more other dashboards further comprises performing a search of metadata of a plurality of dashboards based on the extracted key text portion and selecting the one or more dashboards based on a matching of the key text portion with content in metadata associated with the one or more other dashboards.

24. An apparatus comprising:

a processor; and a memory coupled to the processor, wherein the memory includes instructions which, when executed by the processor, cause the processor to:

present, on a client computing device, a first dashboard providing a graphical user interface to a first user;

track user inputs to the client computing device, at least during and after presentation of the first dashboard to the first user, to identify at least one characteristic of the user inputs;

generate predictive analytics by applying logic to: identify and analyze dashboard usage patterns associated with one or more other users that accessed the first dashboard and transitioned from the first dashboard to one or more other dashboards, and interactions of the one or more other users with portions of the one or more other dashboards, and to identify and analyze user characteristics associated with the one or more other users;

apply predictive analytics to the tracked user inputs to predict a type of data the first user is attempting to access and that is not provided by the first dashboard;

correlate the predicted type of data with the one or more portions of the one or more other dashboards, wherein the one or more portions of the one or more other dashboards provide a representation of data having a type matching the predicted type of data that is not provided by the first dashboard;

output a recommendation to the first user via an interactive graphical user interface element indicating the one or more correlated portions of the one or more other dashboards providing the representation of data matching the predicted type of data that is not provided by the first dashboard;

receive a user selection of the recommendation via the interactive graphical user interface element; and in response to the user selection, modify the first dashboard to display the predicted type of data by incorporating into the first dashboard the one or more correlated portions of from the one or more other dashboards.

* * * * *